United States Patent
Al-Ali et al.

(10) Patent No.: US 10,231,657 B2
(45) Date of Patent: Mar. 19, 2019

(54) TOTAL HEMOGLOBIN SCREENING SENSOR

(71) Applicant: MASIMO CORPORATION, Irvine, CA (US)

(72) Inventors: Ammar Al-Ali, San Juan Capistrano, CA (US); Keith Ward Indorf, Riverside, CA (US)

(73) Assignee: Masimo Corporation, Irvine, CA (US)

( * ) Notice: Subject to any disclaimer, the term of this patent is extended or adjusted under 35 U.S.C. 154(b) by 785 days.

(21) Appl. No.: 14/845,090

(22) Filed: Sep. 3, 2015

(65) Prior Publication Data

US 2016/0066824 A1 Mar. 10, 2016

Related U.S. Application Data

(60) Provisional application No. 62/045,565, filed on Sep. 4, 2014.

(51) Int. Cl.
*A61B 5/1455* (2006.01)
*A61B 5/00* (2006.01)
*A61B 5/0205* (2006.01)

(52) U.S. Cl.
CPC ........ *A61B 5/1455* (2013.01); *A61B 5/14552* (2013.01); *A61B 5/6826* (2013.01); *A61B 5/7221* (2013.01); *A61B 5/7275* (2013.01); *A61B 5/02055* (2013.01); *A61B 5/742* (2013.01); *A61B 5/746* (2013.01); *A61B 2560/0443* (2013.01)

(58) Field of Classification Search
None
See application file for complete search history.

(56) References Cited

U.S. PATENT DOCUMENTS

| | | |
|---|---|---|
| 4,960,128 A | 10/1990 | Gordon et al. |
| 4,964,408 A | 10/1990 | Hink et al. |
| 5,041,187 A | 8/1991 | Hink et al. |
| 5,069,213 A | 12/1991 | Polczynski |
| 5,163,438 A | 11/1992 | Gordon et al. |
| 5,319,355 A | 6/1994 | Russek |
| 5,337,744 A | 8/1994 | Branigan |
| 5,341,805 A | 8/1994 | Stavridi et al. |
| D353,195 S | 12/1994 | Savage et al. |
| D353,196 S | 12/1994 | Savage et al. |
| 5,377,676 A | 1/1995 | Vari et al. |
| D359,546 S | 6/1995 | Savage et al. |
| 5,431,170 A | 7/1995 | Mathews |
| D361,840 S | 8/1995 | Savage et al. |

(Continued)

OTHER PUBLICATIONS

US 8,845,543, 09/2014, Diab et al. (withdrawn)

*Primary Examiner* — Eric F Winakur
*Assistant Examiner* — Marjan Fardanesh
(74) *Attorney, Agent, or Firm* — Knobbe, Martens, Olson & Bear, LLP

(57) ABSTRACT

A total hemoglobin index system derives total hemoglobin (tHb) index value utilizing a depopulated emitter with an index set of LEDs. A patient fails a tHb index test if tHb measurements are trending down and/or tHb values fall below a predefined index threshold. If a patient fails the tHb index test, a high resolution sensor derives a specific tHb measurement utilizing a high resolution set of LEDs. The number of high resolution set LEDs is greater than the number of index set LEDs.

20 Claims, 14 Drawing Sheets

(56) References Cited

U.S. PATENT DOCUMENTS

| | | |
|---|---|---|
| D362,063 S | 9/1995 | Savage et al. |
| 5,452,717 A | 9/1995 | Branigan et al. |
| D363,120 S | 10/1995 | Savage et al. |
| 5,456,252 A | 10/1995 | Vari et al. |
| 5,479,934 A | 1/1996 | Imran |
| 5,482,036 A | 1/1996 | Diab et al. |
| 5,490,505 A | 2/1996 | Diab et al. |
| 5,494,043 A | 2/1996 | O'Sullivan et al. |
| 5,533,511 A | 7/1996 | Kaspari et al. |
| 5,534,851 A | 7/1996 | Russek |
| 5,561,275 A | 10/1996 | Savage et al. |
| 5,562,002 A | 10/1996 | Lalin |
| 5,590,649 A | 1/1997 | Caro et al. |
| 5,602,924 A | 2/1997 | Durand et al. |
| 5,632,272 A | 5/1997 | Diab et al. |
| 5,638,816 A | 6/1997 | Kiani-Azarbayjany et al. |
| 5,638,818 A | 6/1997 | Diab et al. |
| 5,645,440 A | 7/1997 | Tobler et al. |
| 5,685,299 A | 11/1997 | Diab et al. |
| D393,830 S | 4/1998 | Tobler et al. |
| 5,743,262 A | 4/1998 | Lepper, Jr. et al. |
| 5,758,644 A | 6/1998 | Diab et al. |
| 5,760,910 A | 6/1998 | Lepper, Jr. et al. |
| 5,769,785 A | 6/1998 | Diab et al. |
| 5,782,757 A | 7/1998 | Diab et al. |
| 5,785,659 A | 7/1998 | Caro et al. |
| 5,791,347 A | 8/1998 | Flaherty et al. |
| 5,810,734 A | 9/1998 | Caro et al. |
| 5,823,950 A | 10/1998 | Diab et al. |
| 5,830,131 A | 11/1998 | Caro et al. |
| 5,833,618 A | 11/1998 | Caro et al. |
| 5,860,919 A | 1/1999 | Kiani-Azarbayjany et al. |
| 5,890,929 A | 4/1999 | Mills et al. |
| 5,904,654 A | 5/1999 | Wohltmann et al. |
| 5,919,134 A | 7/1999 | Diab |
| 5,934,925 A | 8/1999 | Tobler et al. |
| 5,940,182 A | 8/1999 | Lepper, Jr. et al. |
| 5,995,855 A | 11/1999 | Kiani et al. |
| 5,997,343 A | 12/1999 | Mills et al. |
| 6,002,952 A | 12/1999 | Diab et al. |
| 6,011,986 A | 1/2000 | Diab et al. |
| 6,027,452 A | 2/2000 | Flaherty et al. |
| 6,036,642 A | 3/2000 | Diab et al. |
| 6,045,509 A | 4/2000 | Caro et al. |
| 6,067,462 A | 5/2000 | Diab et al. |
| 6,081,735 A | 6/2000 | Diab et al. |
| 6,088,607 A | 7/2000 | Diab et al. |
| 6,110,522 A | 8/2000 | Lepper, Jr. et al. |
| 6,124,597 A | 9/2000 | Shehada |
| 6,128,521 A | 10/2000 | Marro et al. |
| 6,129,675 A | 10/2000 | Jay |
| 6,144,868 A | 11/2000 | Parker |
| 6,151,516 A | 11/2000 | Kiani-Azarbayjany et al. |
| 6,152,754 A | 11/2000 | Gerhardt et al. |
| 6,157,850 A | 12/2000 | Diab et al. |
| 6,165,005 A | 12/2000 | Mills et al. |
| 6,184,521 B1 | 2/2001 | Coffin, IV et al. |
| 6,206,830 B1 | 3/2001 | Diab et al. |
| 6,229,856 B1 | 5/2001 | Diab et al. |
| 6,232,609 B1 | 5/2001 | Snyder et al. |
| 6,236,872 B1 | 5/2001 | Diab et al. |
| 6,241,683 B1 | 6/2001 | Macklem et al. |
| 6,253,097 B1 | 6/2001 | Aronow et al. |
| 6,256,523 B1 | 7/2001 | Diab et al. |
| 6,263,222 B1 | 7/2001 | Diab et al. |
| 6,278,522 B1 | 8/2001 | Lepper, Jr. et al. |
| 6,280,213 B1 | 8/2001 | Tobler et al. |
| 6,285,896 B1 | 9/2001 | Tobler et al. |
| 6,301,493 B1 | 10/2001 | Marro et al. |
| 6,317,627 B1 | 11/2001 | Ennen et al. |
| 6,321,100 B1 | 11/2001 | Parker |
| 6,325,761 B1 | 12/2001 | Jay |
| 6,334,065 B1 | 12/2001 | Al-Ali et al. |
| 6,343,224 B1 | 1/2002 | Parker |
| 6,349,228 B1 | 2/2002 | Kiani et al. |
| 6,360,114 B1 | 3/2002 | Diab et al. |
| 6,368,283 B1 | 4/2002 | Xu et al. |
| 6,371,921 B1 | 4/2002 | Caro et al. |
| 6,377,829 B1 * | 4/2002 | Al-Ali ............... A61B 5/14552 600/323 |
| 6,388,240 B2 | 5/2002 | Schulz et al. |
| 6,397,091 B2 | 5/2002 | Diab et al. |
| 6,430,437 B1 | 8/2002 | Marro |
| 6,430,525 B1 | 8/2002 | Weber et al. |
| 6,463,311 B1 | 10/2002 | Diab |
| 6,470,199 B1 | 10/2002 | Kopotic et al. |
| 6,501,975 B2 | 12/2002 | Diab et al. |
| 6,505,059 B1 | 1/2003 | Kollias et al. |
| 6,515,273 B2 | 2/2003 | Al-Ali |
| 6,519,487 B1 | 2/2003 | Parker |
| 6,525,386 B1 | 2/2003 | Mills et al. |
| 6,526,300 B1 | 2/2003 | Kiani et al. |
| 6,541,756 B2 | 4/2003 | Schulz et al. |
| 6,542,764 B1 | 4/2003 | Al-Ali et al. |
| 6,580,086 B1 | 6/2003 | Schulz et al. |
| 6,584,336 B1 | 6/2003 | Ali et al. |
| 6,595,316 B2 | 7/2003 | Cybulski et al. |
| 6,597,932 B2 | 7/2003 | Tian et al. |
| 6,597,933 B2 | 7/2003 | Kiani et al. |
| 6,606,511 B1 | 8/2003 | Ali et al. |
| 6,632,181 B2 | 10/2003 | Flaherty et al. |
| 6,639,668 B1 | 10/2003 | Trepagnier |
| 6,640,116 B2 | 10/2003 | Diab |
| 6,643,530 B2 | 11/2003 | Diab et al. |
| 6,650,917 B2 | 11/2003 | Diab et al. |
| 6,654,624 B2 | 11/2003 | Diab et al. |
| 6,658,276 B2 | 12/2003 | Kiani et al. |
| 6,661,161 B1 | 12/2003 | Lanzo et al. |
| 6,671,531 B2 | 12/2003 | Al-Ali et al. |
| 6,678,543 B2 | 1/2004 | Diab et al. |
| 6,684,090 B2 | 1/2004 | Ali et al. |
| 6,684,091 B2 | 1/2004 | Parker |
| 6,697,656 B1 | 2/2004 | Al-Ali |
| 6,697,657 B1 | 2/2004 | Shehada et al. |
| 6,697,658 B2 | 2/2004 | Al-Ali |
| RE38,476 E | 3/2004 | Diab et al. |
| 6,699,194 B1 | 3/2004 | Diab et al. |
| 6,714,804 B2 | 3/2004 | Al-Ali et al. |
| RE38,492 E | 4/2004 | Diab et al. |
| 6,721,582 B2 | 4/2004 | Trepagnier et al. |
| 6,721,585 B1 | 4/2004 | Parker |
| 6,725,075 B2 | 4/2004 | Al-Ali |
| 6,728,560 B2 | 4/2004 | Kollias et al. |
| 6,735,459 B2 | 5/2004 | Parker |
| 6,745,060 B2 | 6/2004 | Diab et al. |
| 6,760,607 B2 | 7/2004 | Al-Ali |
| 6,770,028 B1 | 8/2004 | Ali et al. |
| 6,771,994 B2 | 8/2004 | Kiani et al. |
| 6,792,300 B1 | 9/2004 | Diab et al. |
| 6,813,511 B2 | 11/2004 | Diab et al. |
| 6,816,741 B2 | 11/2004 | Diab |
| 6,822,564 B2 | 11/2004 | Al-Ali |
| 6,826,419 B2 | 11/2004 | Diab et al. |
| 6,830,711 B2 | 12/2004 | Mills et al. |
| 6,850,787 B2 | 2/2005 | Weber et al. |
| 6,850,788 B2 | 2/2005 | Al-Ali |
| 6,852,083 B2 | 2/2005 | Caro et al. |
| 6,861,639 B2 | 3/2005 | Al-Ali |
| 6,898,452 B2 | 5/2005 | Al-Ali et al. |
| 6,920,345 B2 | 7/2005 | Al-Ali et al. |
| 6,931,268 B1 | 8/2005 | Kiani-Azarbayjany et al. |
| 6,934,570 B2 | 8/2005 | Kiani et al. |
| 6,939,305 B2 | 9/2005 | Flaherty et al. |
| 6,943,348 B1 | 9/2005 | Coffin, IV |
| 6,950,687 B2 | 9/2005 | Al-Ali |
| 6,961,598 B2 | 11/2005 | Diab |
| 6,970,792 B1 | 11/2005 | Diab |
| 6,979,812 B2 | 12/2005 | Al-Ali |
| 6,985,764 B2 | 1/2006 | Mason et al. |
| 6,993,371 B2 | 1/2006 | Kiani et al. |
| 6,996,427 B2 | 2/2006 | Ali et al. |
| 6,999,904 B2 | 2/2006 | Weber et al. |
| 7,003,338 B2 | 2/2006 | Weber et al. |
| 7,003,339 B2 | 2/2006 | Diab et al. |

(56) References Cited

U.S. PATENT DOCUMENTS

| | | |
|---|---|---|
| 7,015,451 B2 | 3/2006 | Dalke et al. |
| 7,024,233 B2 | 4/2006 | Ali et al. |
| 7,027,849 B2 | 4/2006 | Al-Ali |
| 7,030,749 B2 | 4/2006 | Al-Ali |
| 7,039,449 B2 | 5/2006 | Al-Ali |
| 7,041,060 B2 | 5/2006 | Flaherty et al. |
| 7,044,918 B2 | 5/2006 | Diab |
| 7,067,893 B2 | 6/2006 | Mills et al. |
| 7,096,052 B2 | 8/2006 | Mason et al. |
| 7,096,054 B2 | 8/2006 | Abdul-Hafiz et al. |
| 7,132,641 B2 | 11/2006 | Schulz et al. |
| 7,142,901 B2 | 11/2006 | Kiani et al. |
| 7,149,561 B2 | 12/2006 | Diab |
| 7,186,966 B2 | 3/2007 | Al-Ali |
| 7,190,261 B2 | 3/2007 | Al-Ali |
| 7,215,984 B2 | 5/2007 | Diab |
| 7,215,986 B2 | 5/2007 | Diab |
| 7,221,971 B2 | 5/2007 | Diab |
| 7,225,006 B2 | 5/2007 | Al-Ali et al. |
| 7,225,007 B2 | 5/2007 | Al-Ali |
| RE39,672 E | 6/2007 | Shehada et al. |
| 7,239,905 B2 | 7/2007 | Kiani-Azarbayjany et al. |
| 7,245,953 B1 | 7/2007 | Parker |
| 7,254,429 B2 | 8/2007 | Schurman et al. |
| 7,254,431 B2 | 8/2007 | Al-Ali |
| 7,254,433 B2 | 8/2007 | Diab et al. |
| 7,254,434 B2 | 8/2007 | Schulz et al. |
| 7,272,425 B2 | 9/2007 | Al-Ali |
| 7,274,955 B2 | 9/2007 | Kiani et al. |
| D554,263 S | 10/2007 | Al-Ali |
| 7,280,858 B2 | 10/2007 | Al-Ali et al. |
| 7,289,835 B2 | 10/2007 | Mansfield et al. |
| 7,292,883 B2 | 11/2007 | De Felice et al. |
| 7,295,866 B2 | 11/2007 | Al-Ali |
| 7,328,053 B1 | 2/2008 | Diab et al. |
| 7,332,784 B2 | 2/2008 | Mills et al. |
| 7,340,287 B2 | 3/2008 | Mason et al. |
| 7,341,559 B2 | 3/2008 | Schulz et al. |
| 7,343,186 B2 | 3/2008 | Lamego et al. |
| D566,282 S | 4/2008 | Al-Ali et al. |
| 7,355,512 B1 | 4/2008 | Al-Ali |
| 7,356,365 B2 | 4/2008 | Schurman |
| 7,371,981 B2 | 5/2008 | Abdul-Hafiz |
| 7,373,193 B2 | 5/2008 | Al-Ali et al. |
| 7,373,194 B2 | 5/2008 | Weber et al. |
| 7,376,453 B1 | 5/2008 | Diab et al. |
| 7,377,794 B2 | 5/2008 | Al Ali et al. |
| 7,377,899 B2 | 5/2008 | Weber et al. |
| 7,383,070 B2 | 6/2008 | Diab et al. |
| 7,415,297 B2 | 8/2008 | Al-Ali et al. |
| 7,428,432 B2 | 9/2008 | Ali et al. |
| 7,438,683 B2 | 10/2008 | Al-Ali et al. |
| 7,440,787 B2 | 10/2008 | Diab |
| 7,454,240 B2 | 11/2008 | Diab et al. |
| 7,467,002 B2 | 12/2008 | Weber et al. |
| 7,469,157 B2 | 12/2008 | Diab et al. |
| 7,471,969 B2 | 12/2008 | Diab et al. |
| 7,471,971 B2 | 12/2008 | Diab et al. |
| 7,483,729 B2 | 1/2009 | Al-Ali et al. |
| 7,483,730 B2 | 1/2009 | Diab et al. |
| 7,489,958 B2 | 2/2009 | Diab et al. |
| 7,496,391 B2 | 2/2009 | Diab et al. |
| 7,496,393 B2 | 2/2009 | Diab et al. |
| D587,657 S | 3/2009 | Al-Ali et al. |
| 7,499,741 B2 | 3/2009 | Diab et al. |
| 7,499,835 B2 | 3/2009 | Weber et al. |
| 7,500,950 B2 | 3/2009 | Al-Ali et al. |
| 7,509,154 B2 | 3/2009 | Diab et al. |
| 7,509,494 B2 | 3/2009 | Al-Ali |
| 7,510,849 B2 | 3/2009 | Schurman et al. |
| 7,526,328 B2 | 4/2009 | Diab et al. |
| 7,530,942 B1 | 5/2009 | Diab |
| 7,530,949 B2 | 5/2009 | Al Ali et al. |
| 7,530,955 B2 | 5/2009 | Diab et al. |
| 7,563,110 B2 | 7/2009 | Al-Ali et al. |
| 7,596,398 B2 | 9/2009 | Al-Ali et al. |
| 7,618,375 B2 | 11/2009 | Flaherty |
| D606,659 S | 12/2009 | Kiani et al. |
| 7,647,083 B2 | 1/2010 | Al-Ali et al. |
| D609,193 S | 2/2010 | Al-Ali et al. |
| D614,305 S | 4/2010 | Al-Ali et al. |
| RE41,317 E | 5/2010 | Parker |
| 7,729,733 B2 | 6/2010 | Al-Ali et al. |
| 7,734,320 B2 | 6/2010 | Al-Ali |
| 7,761,127 B2 | 7/2010 | Al-Ali et al. |
| 7,761,128 B2 | 7/2010 | Al-Ali et al. |
| 7,764,982 B2 | 7/2010 | Dalke et al. |
| D621,516 S | 8/2010 | Kiani et al. |
| 7,791,155 B2 | 9/2010 | Diab |
| 7,801,581 B2 | 9/2010 | Diab |
| 7,822,452 B2 | 10/2010 | Schurman et al. |
| RE41,912 E | 11/2010 | Parker |
| 7,844,313 B2 | 11/2010 | Kiani et al. |
| 7,844,314 B2 | 11/2010 | Al-Ali |
| 7,844,315 B2 | 11/2010 | Al-Ali |
| 7,865,222 B2 | 1/2011 | Weber et al. |
| 7,873,497 B2 | 1/2011 | Weber et al. |
| 7,880,606 B2 | 2/2011 | Al-Ali |
| 7,880,626 B2 | 2/2011 | Al-Ali et al. |
| 7,891,355 B2 | 2/2011 | Al-Ali et al. |
| 7,894,868 B2 | 2/2011 | Al-Ali et al. |
| 7,899,507 B2 | 3/2011 | Al-Ali et al. |
| 7,899,518 B2 | 3/2011 | Trepagnier et al. |
| 7,904,132 B2 | 3/2011 | Weber et al. |
| 7,909,772 B2 | 3/2011 | Popov et al. |
| 7,910,875 B2 | 3/2011 | Al-Ali |
| 7,919,713 B2 | 4/2011 | Al-Ali et al. |
| 7,937,128 B2 | 5/2011 | Al-Ali |
| 7,937,129 B2 | 5/2011 | Mason et al. |
| 7,937,130 B2 | 5/2011 | Diab et al. |
| 7,941,199 B2 | 5/2011 | Kiani |
| 7,951,086 B2 | 5/2011 | Flaherty et al. |
| 7,957,780 B2 | 6/2011 | Lamego et al. |
| 7,962,188 B2 | 6/2011 | Kiani et al. |
| 7,962,190 B1 | 6/2011 | Diab et al. |
| 7,976,472 B2 | 7/2011 | Kiani |
| 7,988,637 B2 | 8/2011 | Diab |
| 7,990,382 B2 | 8/2011 | Kiani |
| 7,991,446 B2 | 8/2011 | Al-Ali et al. |
| 8,000,761 B2 | 8/2011 | Al-Ali |
| 8,008,088 B2 | 8/2011 | Bellott et al. |
| RE42,753 E | 9/2011 | Kiani-Azarbayjany et al. |
| 8,019,400 B2 | 9/2011 | Diab et al. |
| 8,028,701 B2 | 10/2011 | Al-Ali et al. |
| 8,029,765 B2 | 10/2011 | Bellott et al. |
| 8,036,727 B2 | 10/2011 | Schurman et al. |
| 8,036,728 B2 | 10/2011 | Diab et al. |
| 8,046,040 B2 | 10/2011 | Ali et al. |
| 8,046,041 B2 | 10/2011 | Diab et al. |
| 8,046,042 B2 | 10/2011 | Diab et al. |
| 8,048,040 B2 | 11/2011 | Kiani |
| 8,050,728 B2 | 11/2011 | Al-Ali et al. |
| RE43,169 E | 2/2012 | Parker |
| 8,118,620 B2 | 2/2012 | Al-Ali et al. |
| 8,126,528 B2 | 2/2012 | Diab et al. |
| 8,128,572 B2 | 3/2012 | Diab et al. |
| 8,130,105 B2 | 3/2012 | Al-Ali et al. |
| 8,145,287 B2 | 3/2012 | Diab et al. |
| 8,150,487 B2 | 4/2012 | Diab et al. |
| 8,175,672 B2 | 5/2012 | Parker |
| 8,180,420 B2 | 5/2012 | Diab et al. |
| 8,182,443 B1 | 5/2012 | Kiani |
| 8,185,180 B2 | 5/2012 | Diab et al. |
| 8,190,223 B2 | 5/2012 | Al-Ali et al. |
| 8,190,227 B2 | 5/2012 | Diab et al. |
| 8,203,438 B2 | 6/2012 | Kiani et al. |
| 8,203,704 B2 | 6/2012 | Merritt et al. |
| 8,204,566 B2 | 6/2012 | Schurman et al. |
| 8,219,172 B2 | 7/2012 | Schurman et al. |
| 8,224,411 B2 | 7/2012 | Al-Ali et al. |
| 8,228,181 B2 | 7/2012 | Al-Ali |
| 8,229,533 B2 | 7/2012 | Diab et al. |
| 8,233,955 B2 | 7/2012 | Al-Ali et al. |
| 8,244,325 B2 | 8/2012 | Al-Ali et al. |

(56) References Cited

U.S. PATENT DOCUMENTS

| | | |
|---|---|---|
| 8,255,026 B1 | 8/2012 | Al-Ali |
| 8,255,027 B2 | 8/2012 | Al-Ali et al. |
| 8,255,028 B2 | 8/2012 | Al-Ali et al. |
| 8,260,577 B2 | 9/2012 | Weber et al. |
| 8,265,723 B1 | 9/2012 | McHale et al. |
| 8,274,360 B2 | 9/2012 | Sampath et al. |
| 8,301,217 B2 | 10/2012 | Al-Ali et al. |
| 8,306,596 B2 | 11/2012 | Schurman et al. |
| 8,310,336 B2 | 11/2012 | Muhsin et al. |
| 8,315,683 B2 | 11/2012 | Al-Ali et al. |
| RE43,860 E | 12/2012 | Parker |
| 8,337,403 B2 | 12/2012 | Al-Ali et al. |
| 8,346,330 B2 | 1/2013 | Lamego |
| 8,353,842 B2 | 1/2013 | Al-Ali et al. |
| 8,355,766 B2 | 1/2013 | MacNeish, III et al. |
| 8,359,080 B2 | 1/2013 | Diab et al. |
| 8,364,223 B2 | 1/2013 | Al-Ali et al. |
| 8,364,226 B2 | 1/2013 | Diab et al. |
| 8,374,665 B2 | 2/2013 | Lamego |
| 8,385,995 B2 | 2/2013 | Al-ali et al. |
| 8,385,996 B2 | 2/2013 | Smith et al. |
| 8,388,353 B2 | 3/2013 | Kiani et al. |
| 8,399,822 B2 | 3/2013 | Al-Ali |
| 8,401,602 B2 | 3/2013 | Kiani |
| 8,405,608 B2 | 3/2013 | Al-Ali et al. |
| 8,414,499 B2 | 4/2013 | Al-Ali et al. |
| 8,418,524 B2 | 4/2013 | Al-Ali |
| 8,423,106 B2 | 4/2013 | Lamego et al. |
| 8,428,967 B2 | 4/2013 | Olsen et al. |
| 8,430,817 B1 | 4/2013 | Al-Ali et al. |
| 8,437,825 B2 | 5/2013 | Dalvi et al. |
| 8,455,290 B2 | 6/2013 | Siskavich |
| 8,457,703 B2 | 6/2013 | Al-Ali |
| 8,457,707 B2 | 6/2013 | Kiani |
| 8,463,349 B2 | 6/2013 | Diab et al. |
| 8,466,286 B2 | 6/2013 | Bellot et al. |
| 8,471,713 B2 | 6/2013 | Poeze et al. |
| 8,473,020 B2 | 6/2013 | Kiani et al. |
| 8,483,787 B2 | 7/2013 | Al-Ali et al. |
| 8,489,364 B2 | 7/2013 | Weber et al. |
| 8,498,684 B2 | 7/2013 | Weber et al. |
| 8,504,128 B2 | 8/2013 | Blank et al. |
| 8,509,867 B2 | 8/2013 | Workman et al. |
| 8,515,509 B2 | 8/2013 | Bruinsma et al. |
| 8,523,781 B2 | 9/2013 | Al-Ali |
| 8,529,301 B2 | 9/2013 | Al-Ali et al. |
| 8,532,727 B2 | 9/2013 | Ali et al. |
| 8,532,728 B2 | 9/2013 | Diab et al. |
| D692,145 S | 10/2013 | Al-Ali et al. |
| 8,547,209 B2 | 10/2013 | Kiani et al. |
| 8,548,548 B2 | 10/2013 | Al-Ali |
| 8,548,549 B2 | 10/2013 | Schurman et al. |
| 8,548,550 B2 | 10/2013 | Al-Ali et al. |
| 8,560,032 B2 | 10/2013 | Al-Ali et al. |
| 8,560,034 B1 | 10/2013 | Diab et al. |
| 8,570,167 B2 | 10/2013 | Al-Ali |
| 8,570,503 B2 | 10/2013 | Vo et al. |
| 8,571,617 B2 | 10/2013 | Reichgott et al. |
| 8,571,618 B1 | 10/2013 | Lamego et al. |
| 8,571,619 B2 | 10/2013 | Al-Ali et al. |
| 8,584,345 B2 | 10/2013 | Al-Ali et al. |
| 8,577,431 B2 | 11/2013 | Lamego et al. |
| 8,581,732 B2 | 11/2013 | Al-Ali et al. |
| 8,588,880 B2 | 11/2013 | Abdul-Hafiz et al. |
| 8,600,467 B2 | 12/2013 | Al-Ali et al. |
| 8,606,342 B2 | 12/2013 | Diab |
| 8,626,255 B2 | 1/2014 | Al-Ali et al. |
| 8,630,691 B2 | 1/2014 | Lamego et al. |
| 8,634,889 B2 | 1/2014 | Al-Ali et al. |
| 8,641,631 B2 | 2/2014 | Sierra et al. |
| 8,652,060 B2 | 2/2014 | Al-Ali |
| 8,663,107 B2 | 3/2014 | Kiani |
| 8,666,468 B1 | 3/2014 | Al-Ali |
| 8,667,967 B2 | 3/2014 | Al-Ali et al. |
| 8,670,811 B2 | 3/2014 | O'Reilly |
| 8,670,814 B2 | 3/2014 | Diab et al. |
| 8,676,286 B2 | 3/2014 | Weber et al. |
| 8,682,407 B2 | 3/2014 | Al-Ali |
| RE44,823 E | 4/2014 | Parker |
| RE44,875 E | 4/2014 | Kiani et al. |
| 8,690,799 B2 | 4/2014 | Telfort et al. |
| 8,700,112 B2 | 4/2014 | Kiani |
| 8,702,627 B2 | 4/2014 | Telfort et al. |
| 8,706,179 B2 | 4/2014 | Parker |
| 8,712,494 B1 | 4/2014 | MacNeish, III et al. |
| 8,715,206 B2 | 5/2014 | Telfort et al. |
| 8,718,735 B2 | 5/2014 | Lamego et al. |
| 8,718,737 B2 | 5/2014 | Diab et al. |
| 8,718,738 B2 | 5/2014 | Blank et al. |
| 8,720,249 B2 | 5/2014 | Al-Ali |
| 8,721,541 B2 | 5/2014 | Al-Ali et al. |
| 8,721,542 B2 | 5/2014 | Al-Ali et al. |
| 8,723,677 B1 | 5/2014 | Kiani |
| 8,740,792 B1 | 6/2014 | Kiani et al. |
| 8,754,776 B2 | 6/2014 | Poeze et al. |
| 8,755,535 B2 | 6/2014 | Telfort et al. |
| 8,755,856 B2 | 6/2014 | Diab et al. |
| 8,755,872 B1 | 6/2014 | Marinow |
| 8,761,850 B2 | 6/2014 | Lamego |
| 8,764,671 B2 | 7/2014 | Kiani |
| 8,768,423 B2 | 7/2014 | Shakespeare et al. |
| 8,771,204 B2 | 7/2014 | Telfort et al. |
| 8,777,634 B2 | 7/2014 | Kiani et al. |
| 8,781,543 B2 | 7/2014 | Diab et al. |
| 8,781,544 B2 | 7/2014 | Al-Ali et al. |
| 8,781,549 B2 | 7/2014 | Al-Ali et al. |
| 8,788,003 B2 | 7/2014 | Schurman et al. |
| 8,790,268 B2 | 7/2014 | Al-Ali |
| 8,801,613 B2 | 8/2014 | Al-Ali et al. |
| 8,821,397 B2 | 9/2014 | Al-Ali et al. |
| 8,821,415 B2 | 9/2014 | Al-Ali et al. |
| 8,830,449 B1 | 9/2014 | Lamego et al. |
| 8,831,700 B2 | 9/2014 | Schurman et al. |
| 8,840,549 B2 | 9/2014 | Al-Ali et al. |
| 8,847,740 B2 | 9/2014 | Kiani et al. |
| 8,849,365 B2 | 9/2014 | Smith et al. |
| 8,852,094 B2 | 10/2014 | Al-Ali et al. |
| 8,852,994 B2 | 10/2014 | Wojtczuk et al. |
| 8,868,147 B2 | 10/2014 | Stippick et al. |
| 8,868,150 B2 | 10/2014 | Al-Ali et al. |
| 8,870,792 B2 | 10/2014 | Al-Ali et al. |
| 8,886,271 B2 | 11/2014 | Kiani et al. |
| 8,888,539 B2 | 11/2014 | Al-Ali et al. |
| 8,888,708 B2 | 11/2014 | Diab et al. |
| 8,892,180 B2 | 11/2014 | Weber et al. |
| 8,897,847 B2 | 11/2014 | Al-Ali |
| 8,909,310 B2 | 12/2014 | Lamego et al. |
| 8,911,377 B2 | 12/2014 | Al-Ali |
| 8,912,909 B2 | 12/2014 | Al-Ali et al. |
| 8,920,317 B2 | 12/2014 | Al-Ali et al. |
| 8,921,699 B2 | 12/2014 | Al-Ali et al. |
| 8,922,382 B2 | 12/2014 | Al-Ali et al. |
| 8,929,964 B2 | 1/2015 | Al-Ali et al. |
| 8,942,777 B2 | 1/2015 | Diab et al. |
| 8,948,834 B2 | 2/2015 | Diab et al. |
| 8,948,835 B2 | 2/2015 | Diab |
| 8,965,471 B2 | 2/2015 | Lamego |
| 8,983,564 B2 | 3/2015 | Al-Ali |
| 8,989,831 B2 | 3/2015 | Al-Ali et al. |
| 8,996,085 B2 | 3/2015 | Kiani et al. |
| 8,998,809 B2 | 4/2015 | Kiani |
| 9,028,429 B2 | 5/2015 | Telfort et al. |
| 9,037,207 B2 | 5/2015 | Al-Ali et al. |
| 9,060,721 B2 | 6/2015 | Reichgott et al. |
| 9,066,666 B2 | 6/2015 | Kiani |
| 9,066,680 B1 | 6/2015 | Al-Ali et al. |
| 9,072,474 B2 | 7/2015 | Al-Ali et al. |
| 9,078,560 B2 | 7/2015 | Schurman et al. |
| 9,084,569 B2 | 7/2015 | Weber et al. |
| 9,095,316 B2 | 8/2015 | Welch et al. |
| 9,106,038 B2 | 8/2015 | Telfort et al. |
| 9,107,625 B2 | 8/2015 | Telfort et al. |
| 9,107,626 B2 | 8/2015 | Al-Ali et al. |
| 9,113,831 B2 | 8/2015 | Al-Ali |

(56) References Cited

U.S. PATENT DOCUMENTS

| | | |
|---|---|---|
| 9,113,832 B2 | 8/2015 | Al-Ali |
| 9,119,595 B2 | 9/2015 | Lamego |
| 2001/0007360 A1* | 7/2001 | Yoshida .............. H01L 25/0753 257/89 |
| 2009/0247984 A1 | 10/2009 | Lamego et al. |
| 2009/0275844 A1 | 11/2009 | Al-Ali |
| 2010/0004518 A1* | 1/2010 | Vo ....................... A61B 5/14532 600/310 |
| 2010/0030040 A1 | 2/2010 | Poeze et al. |
| 2010/0261979 A1 | 10/2010 | Kiani |
| 2010/0317937 A1* | 12/2010 | Kuhn .................. A61B 5/0084 600/323 |
| 2011/0001605 A1 | 1/2011 | Kiani et al. |
| 2011/0082711 A1 | 4/2011 | Poeze et al. |
| 2011/0105854 A1 | 5/2011 | Kiani et al. |
| 2011/0208015 A1 | 8/2011 | Welch et al. |
| 2011/0213212 A1 | 9/2011 | Al-Ali |
| 2011/0230733 A1 | 9/2011 | Al-Ali |
| 2011/0237911 A1 | 9/2011 | Lamego et al. |
| 2012/0059267 A1 | 3/2012 | Lamego et al. |
| 2012/0116175 A1 | 5/2012 | Al-Ali et al. |
| 2012/0179006 A1 | 7/2012 | Jansen et al. |
| 2012/0209082 A1 | 8/2012 | Al-Ali |
| 2012/0209084 A1 | 8/2012 | Olsen et al. |
| 2012/0227739 A1 | 9/2012 | Kiani |
| 2012/0283524 A1 | 11/2012 | Kiani et al. |
| 2012/0296178 A1 | 11/2012 | Lamego et al. |
| 2012/0319816 A1 | 12/2012 | Al-Ali |
| 2012/0330112 A1 | 12/2012 | Lamego et al. |
| 2013/0023775 A1 | 1/2013 | Lamego et al. |
| 2013/0045685 A1 | 2/2013 | Kiani |
| 2013/0046204 A1 | 2/2013 | Lamego et al. |
| 2013/0041591 A1 | 3/2013 | Lamego |
| 2013/0060147 A1 | 3/2013 | Welch et al. |
| 2013/0096405 A1 | 4/2013 | Garfio |
| 2013/0096936 A1 | 4/2013 | Sampath et al. |
| 2013/0109935 A1 | 5/2013 | Al-Ali et al. |
| 2013/0162433 A1 | 6/2013 | Muhsin et al. |
| 2013/0190581 A1 | 7/2013 | Al-Ali et al. |
| 2013/0197328 A1 | 8/2013 | Diab et al. |
| 2013/0211214 A1 | 8/2013 | Olsen |
| 2013/0243021 A1 | 9/2013 | Siskavich |
| 2013/0253334 A1 | 9/2013 | Al-Ali et al. |
| 2013/0274571 A1 | 10/2013 | Diab et al. |
| 2013/0296672 A1 | 11/2013 | O'Neil et al. |
| 2013/0317370 A1 | 11/2013 | Dalvi et al. |
| 2013/0324808 A1 | 12/2013 | Al-Ali et al. |
| 2013/0331670 A1 | 12/2013 | Kiani |
| 2013/0338461 A1 | 12/2013 | Lamego et al. |
| 2014/0012100 A1 | 1/2014 | Al-Ali et al. |
| 2014/0025306 A1 | 1/2014 | Weber et al. |
| 2014/0034353 A1 | 2/2014 | Al-Ali et al. |
| 2014/0051953 A1 | 2/2014 | Lamego et al. |
| 2014/0058230 A1 | 2/2014 | Abdul-Hafiz et al. |
| 2014/0066783 A1 | 3/2014 | Kiani et al. |
| 2014/0077956 A1 | 3/2014 | Sampath et al. |
| 2014/0081100 A1 | 3/2014 | Muhsin et al. |
| 2014/0081175 A1 | 3/2014 | Telfort |
| 2014/0094667 A1 | 4/2014 | Schurman et al. |
| 2014/0100434 A1 | 4/2014 | Diab et al. |
| 2014/0114199 A1 | 4/2014 | Lamego et al. |
| 2014/0120564 A1 | 5/2014 | Workman et al. |
| 2014/0121482 A1 | 5/2014 | Merritt et al. |
| 2014/0121483 A1 | 5/2014 | Kiani |
| 2014/0127137 A1 | 5/2014 | Bellott et al. |
| 2014/0128696 A1 | 5/2014 | Al-Ali |
| 2014/0128699 A1 | 5/2014 | Al-Ali et al. |
| 2014/0129702 A1 | 5/2014 | Lamego et al. |
| 2014/0135588 A1 | 5/2014 | Al-Ali et al. |
| 2014/0142401 A1 | 5/2014 | Al-Ali et al. |
| 2014/0142402 A1 | 5/2014 | Al-Ali et al. |
| 2014/0163344 A1 | 6/2014 | Al-Ali |
| 2014/0163402 A1 | 6/2014 | Lamego et al. |
| 2014/0166076 A1 | 6/2014 | Kiani et al. |
| 2014/0171763 A1 | 6/2014 | Diab |
| 2014/0180038 A1 | 6/2014 | Kiani |
| 2014/0180154 A1 | 6/2014 | Sierra et al. |
| 2014/0194709 A1 | 7/2014 | Al-Ali et al. |
| 2014/0194711 A1 | 7/2014 | Al-Ali |
| 2014/0194766 A1 | 7/2014 | Al-Ali et al. |
| 2014/0206963 A1 | 7/2014 | Al-Ali |
| 2014/0213864 A1 | 7/2014 | Abdul-Hafiz et al. |
| 2014/0243627 A1 | 8/2014 | Diab et al. |
| 2014/0266790 A1 | 9/2014 | Al-Ali et al. |
| 2014/0275808 A1 | 9/2014 | Poeze et al. |
| 2014/0275835 A1 | 9/2014 | Lamego et al. |
| 2014/0275871 A1 | 9/2014 | Lamego et al. |
| 2014/0275872 A1 | 9/2014 | Merritt et al. |
| 2014/0275881 A1 | 9/2014 | Lamego et al. |
| 2014/0288400 A1 | 9/2014 | Diab et al. |
| 2014/0296664 A1 | 10/2014 | Bruinsma et al. |
| 2014/0303520 A1 | 10/2014 | Telfort et al. |
| 2014/0309506 A1 | 10/2014 | Lamego et al. |
| 2014/0316228 A1 | 10/2014 | Blank et al. |
| 2014/0323825 A1 | 10/2014 | Al-Ali et al. |
| 2014/0330092 A1 | 11/2014 | Al-Ali et al. |
| 2014/0330098 A1 | 11/2014 | Merritt et al. |
| 2014/0330099 A1 | 11/2014 | Al-Ali et al. |
| 2014/0333440 A1 | 11/2014 | Kiani |
| 2014/0336481 A1 | 11/2014 | Shakespeare et al. |
| 2014/0343436 A1 | 11/2014 | Kiani |
| 2015/0018650 A1 | 1/2015 | Al-Ali et al. |

* cited by examiner

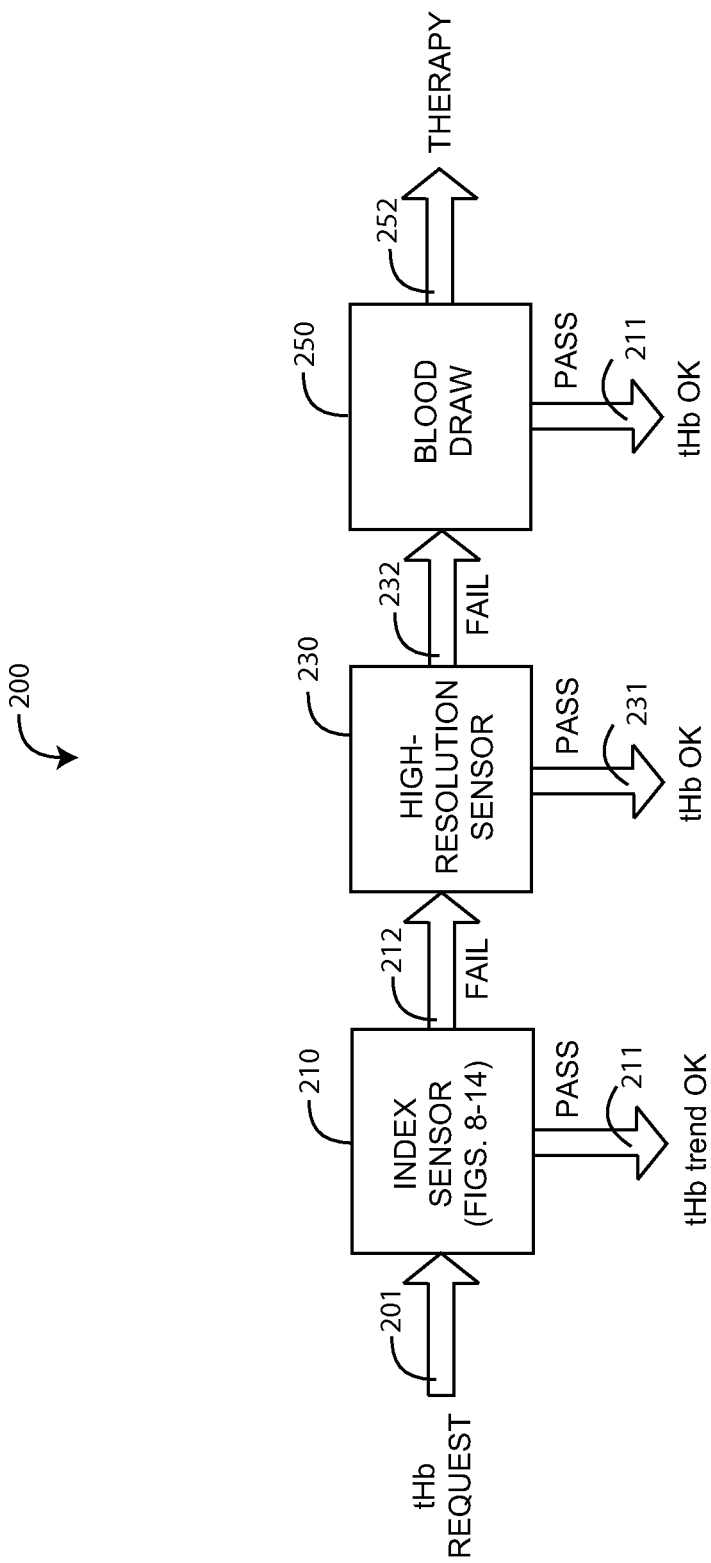

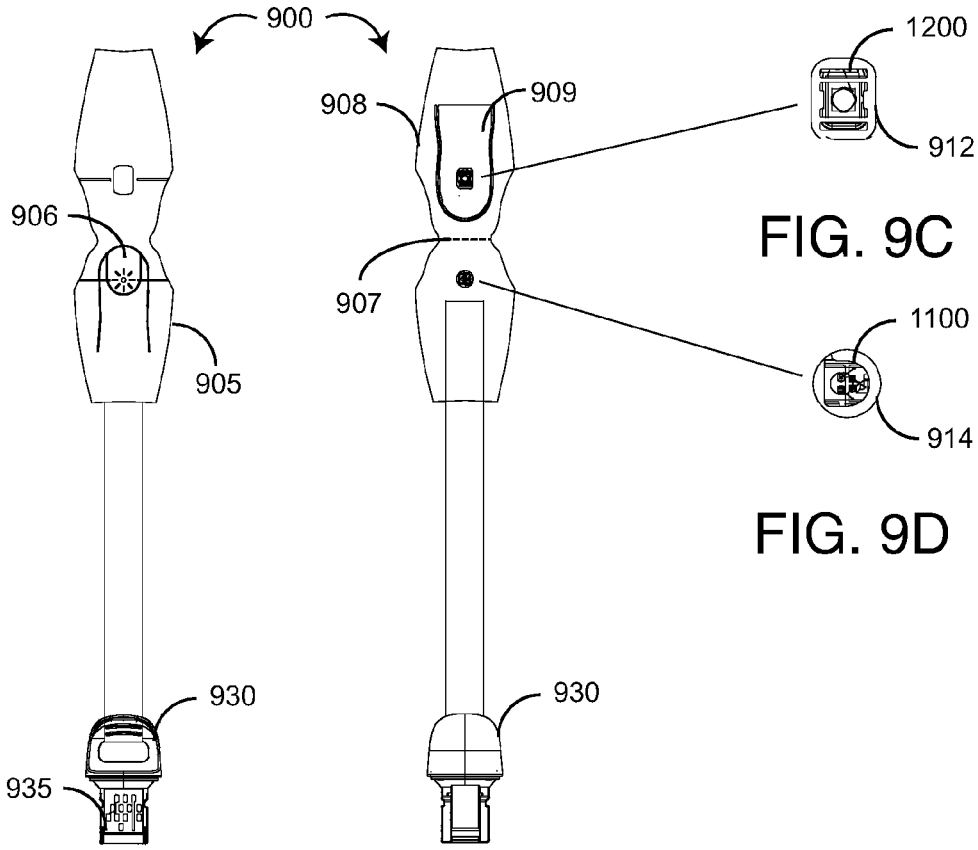
FIG. 9C
FIG. 9D
FIG. 9A   FIG. 9B
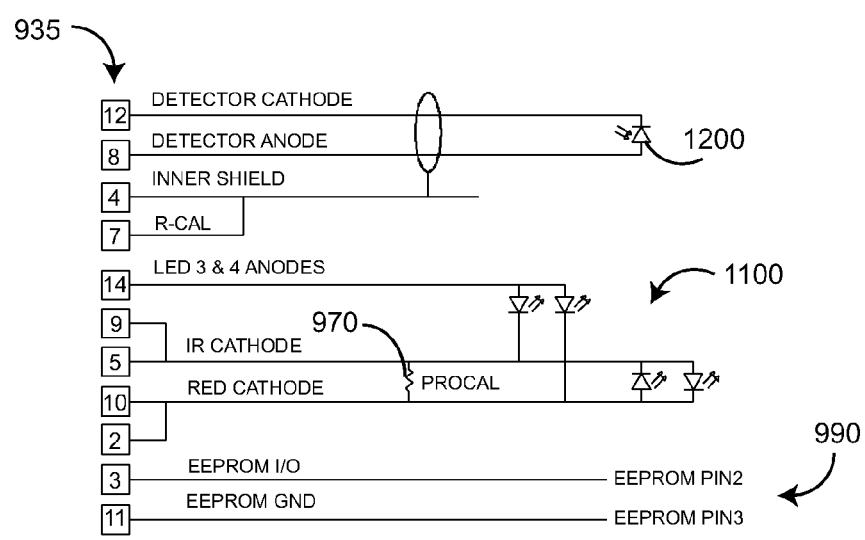
FIG. 9E

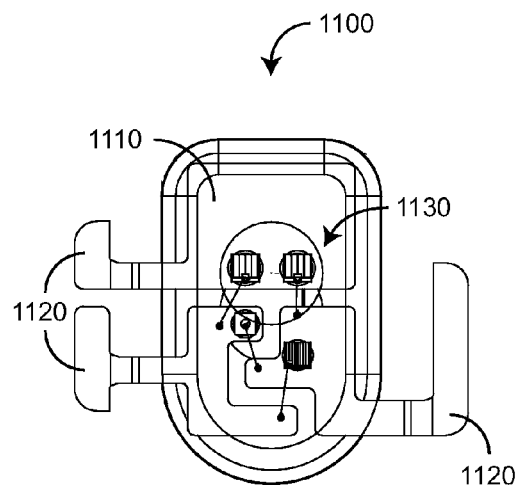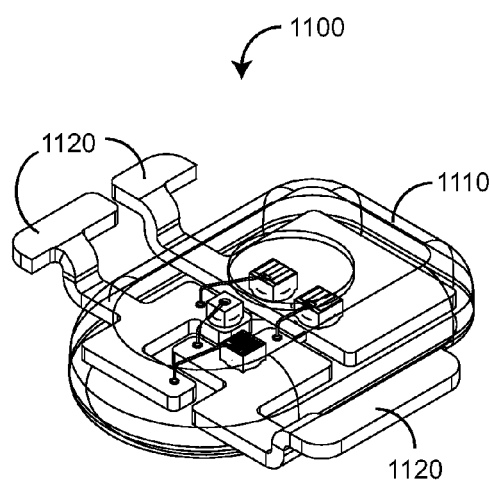
FIG. 11A  FIG. 11B
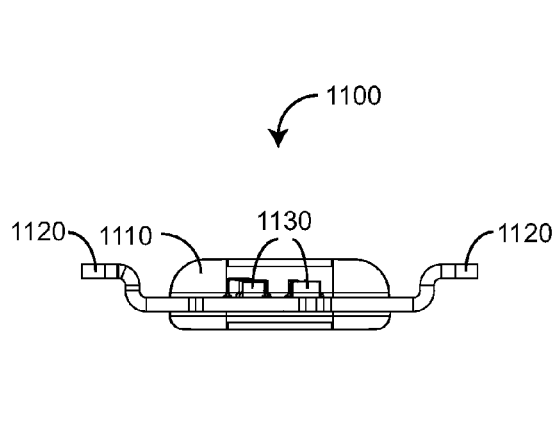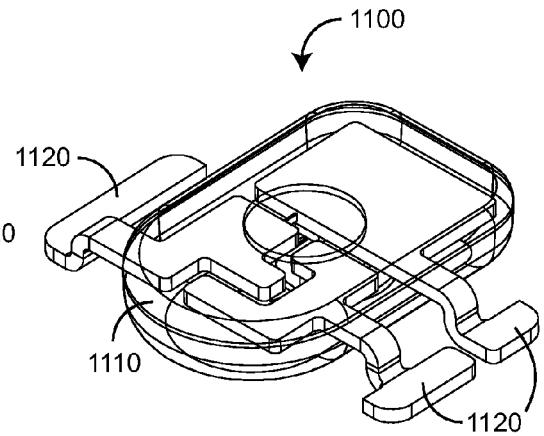
FIG. 11C  FIG. 11D

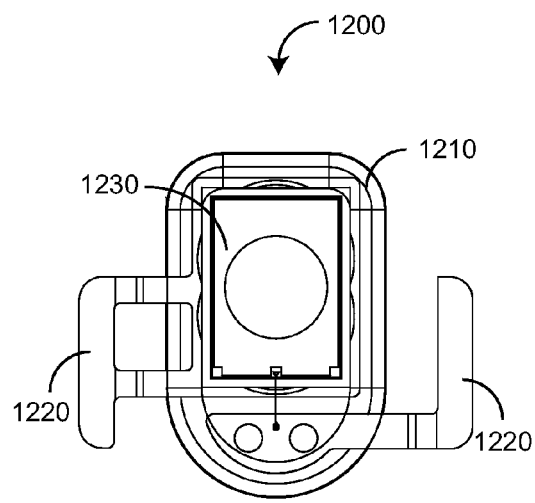
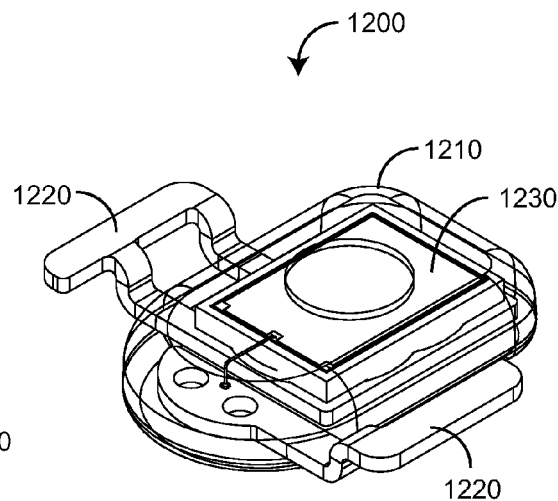
FIG. 12A  FIG. 12B
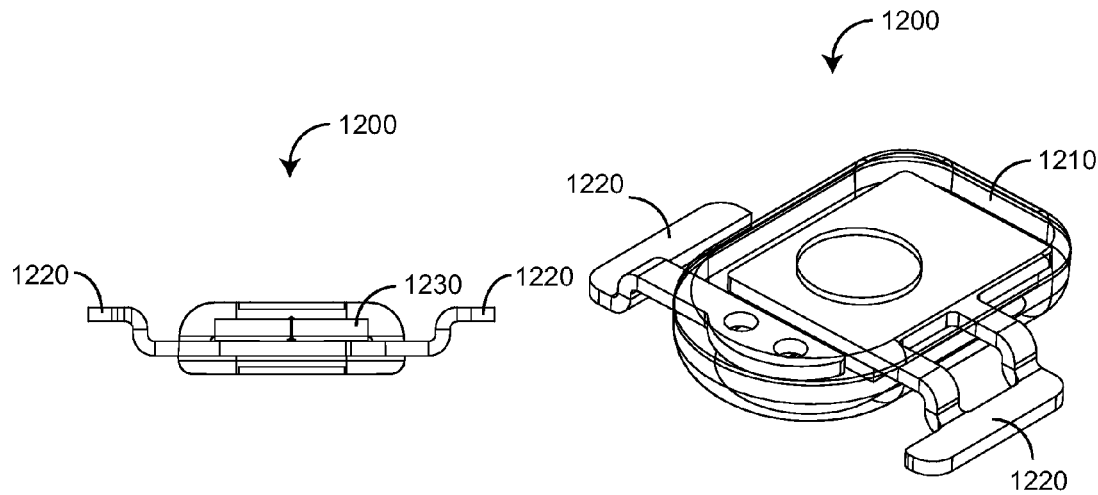
FIG. 12C  FIG. 12D

TOTAL HEMOGLOBIN SCREENING SENSOR

PRIORITY CLAIM TO RELATED PROVISIONAL APPLICATIONS

The present application claims priority benefit under 35 U.S.C. § 119(e) to U.S. Provisional Patent Application Ser. No. 62/045,565 filed Sep. 4, 2014, titled Total Hemoglobin Screening Sensor, hereby incorporated in its entirety by reference herein.

BACKGROUND OF THE INVENTION

Pulse oximetry systems for measuring constituents of circulating blood have gained rapid acceptance in a wide variety of medical applications, including surgical wards, intensive care and neonatal units, general wards, home care, physical training, and virtually all types of monitoring scenarios. A pulse oximetry system generally includes an optical sensor applied to a patient, a monitor for processing sensor signals and displaying results and a patient cable electrically interconnecting the sensor and the monitor. A pulse oximetry sensor has light emitting diodes (LEDs), typically one emitting a red wavelength and one emitting an infrared (IR) wavelength, and a photodiode detector. The emitters and detector are attached to a patient tissue site, such as a finger. The patient cable transmits drive signals to these emitters from the monitor, and the emitters respond to the drive signals to transmit light into the tissue site. The detector generates a signal responsive to the emitted light after attenuation by pulsatile blood flow within the tissue site. The patient cable transmits the detector signal to the monitor, which processes the signal to provide a numerical readout of physiological parameters such as oxygen saturation ($SpO_2$) and pulse rate. Advanced physiological monitoring systems utilize multiple wavelength sensors and multiple parameter monitors to provide enhanced measurement capabilities including, for example, the measurement of carboxyhemoglobin (HbCO), methemoglobin (HbMet) and total hemoglobin (tHb).

Pulse oximeters capable of reading through motion induced noise are disclosed in at least U.S. Pat. Nos. 6,770,028, 6,658,276, 6,650,917, 6,157,850, 6,002,952, 5,769,785, and 5,758,644; low noise pulse oximetry sensors are disclosed in at least U.S. Pat. Nos. 6,088,607 and 5,782,757; all of which are assigned to Masimo Corporation, Irvine, Calif. ("Masimo") and are incorporated in their entireties by reference herein.

Physiological monitors and corresponding multiple wavelength optical sensors are described in at least U.S. patent application Ser. No. 11/367,013, filed Mar. 1, 2006 and entitled Multiple Wavelength Sensor Emitters and U.S. patent application Ser. No. 11/366,208, filed Mar. 1, 2006 and entitled Noninvasive Multi-Parameter Patient Monitor, both assigned to Cercacor Laboratories, Irvine, Calif. (Cercacor) and both incorporated in their entireties by reference herein.

Further, physiological monitoring systems that include low noise optical sensors and pulse oximetry monitors, such as any of LNOP® adhesive or reusable sensors, SofTouch™ sensors, Hi-Fi Trauma™ or Blue™ sensors; and any of Radical®, SatShare™, Rad-9™, Rad-S™, Rad-5v™ or PPO+™ Masimo SET® pulse oximeters, are all available from Masimo. Physiological monitoring systems including multiple wavelength sensors and corresponding noninvasive blood parameter monitors, such as Rainbow™ adhesive and reusable sensors and RAD-57™ and Radical7™ monitors for measuring $SpO_2$, pulse rate, perfusion index, signal quality, HbCO and HbMet among other parameters are also available from Masimo.

SUMMARY OF THE INVENTION

Occult bleeding is frequent in surgery, intensive care and obstetrics, and late detection increases the corresponding risks of serious injury or death. Bleeding alone is responsible for 19% of in-hospital maternal deaths. Further, bleeding significantly increases the total cost of patient treatment. Total hemoglobin (tHb) measurements identify almost 90% of patients with bleeding, but traditional lab measurements are infrequent and delayed. Advantageously, a tHb index system is an aid to clinicians in intensive care units and labor and delivery wards to detect occult bleeding.

Traditional invasive lab testing provides delayed results and requires a painful needle stick and time-consuming blood draws. A total hemoglobin (tHb) index system incorporating an advantageous noninvasive, disposable sensor and a monitor advantageously calculating and displaying a tHb index facilitates timely patient assessment and reduces the need to wait for lab results.

Also, noninvasive tHb monitoring advantageously provides real-time visibility to changes, or lack of changes, in total hemoglobin between invasive blood sampling. Continuous, real-time tHb monitoring is particularly advantageous when a tHb trend is stable and a clinician may otherwise think tHb is dropping; a tHb trend is rising and the clinician may otherwise think tHb is not rising fast enough; or the tHb trend is dropping and the clinician may otherwise think tHb is stable.

Further, a tHb index system decreases the risk of accidental needle sticks and exposure to blood-borne pathogens. In addition, a disposable tHb sensor requires no lab consumables or waste disposal, reduces painful needle sticks and time-consuming blood draws and enables immediate face-to-face counseling with a clinician. The advantages of a tHb index system are enhanced through the use of a low-cost tHb index sensor embodiment utilizing a reduced number of LEDs in the emitter, as described below.

BRIEF DESCRIPTION OF THE DRAWINGS

FIG. 2 is a general flow diagram of tHb index monitoring utilizing a combination of optical sensors including an index sensor and a high-resolution sensor;

FIGS. 9A-E are top and bottom head tape assembly views, enlarged detector window and emitter window views and a connector schematic view, respectively, of a tHb index sensor.

FIGS. 11A-D are top, top-perspective, side and bottom-perspective views, respectively, of a tHb sensor emitter assembly;

FIGS. 12A-D are top, top-perspective, side and bottom-perspective views, respectively, of a tHb sensor detector assembly;

DETAILED DESCRIPTION OF THE PREFERRED EMBODIMENTS

Figure 1:
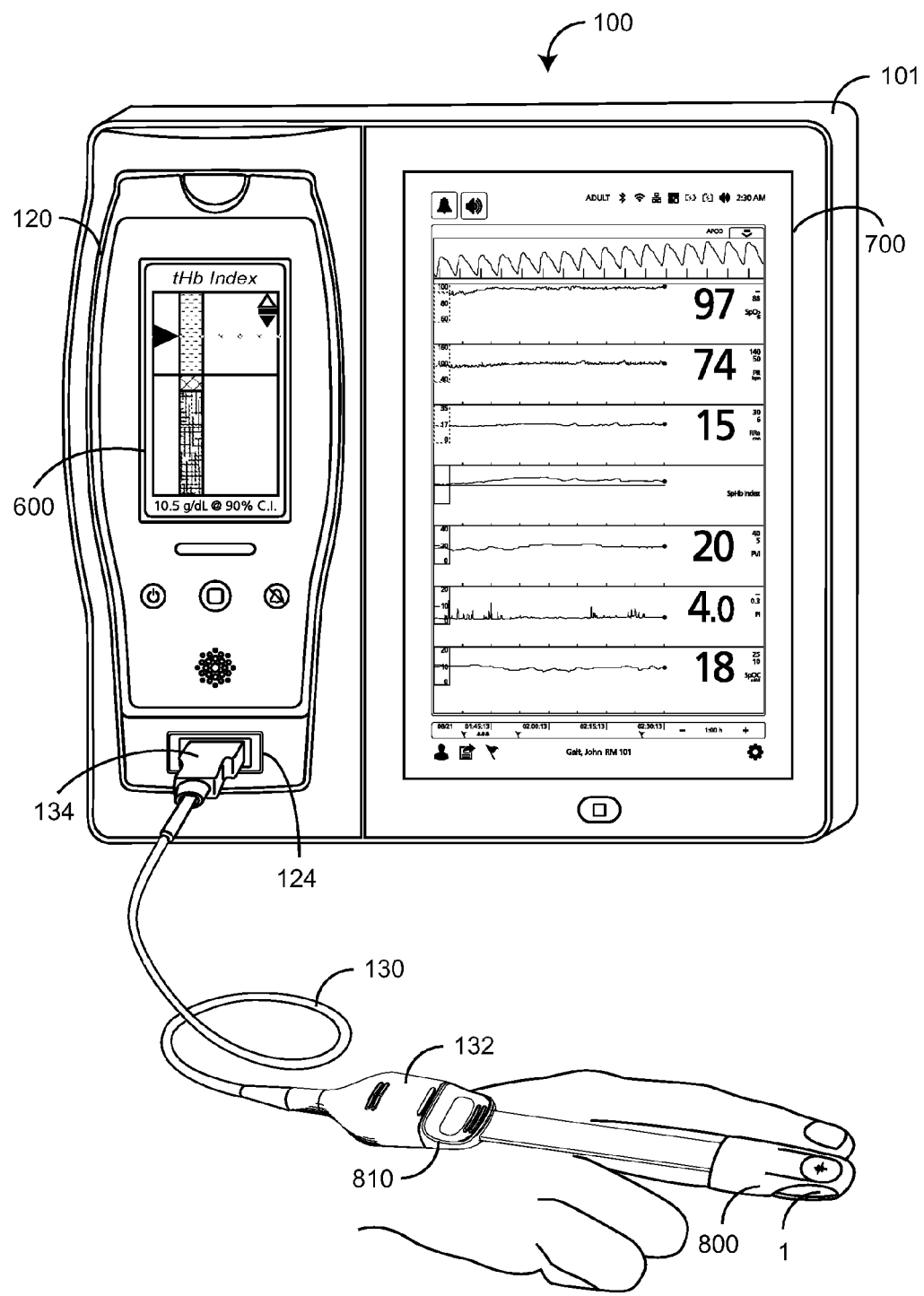
FIG. 1 illustrates a total hemoglobin index system including a total hemoglobin (tHb) index monitor and a corresponding disposable tHb index optical sensor responsive to pulsatile blood flow within a fingertip.

FIG. 1 illustrates a total hemoglobin (tHb) index system 100 including a standalone monitor 101, a portable handheld monitor 120 and a disposable optical sensor 800. The standalone monitor 101 has a main display 700 and the removable handheld monitor 120 has a handheld display 600. The optical sensor 800 attaches to a fingertip 1 so as to optically analyze blood constituents therein, including tHb and others described with respect to FIG. 7, below. In a particular embodiment, the sensor 800 has emitters (LEDs) capable of irradiating the tissue site 1 with multiple wavelengths of light and corresponding detectors capable of detecting the light after attenuation by pulsatile blood flow within the tissue site 1. The sensor 800 removably connects to a patient cable 130, which connects to the monitor 101. In particular, the patient cable 130 has a sensor-side connector 132 that removably attaches to and electrically communicates with the sensor connector 810 and a monitor-side connector 134 that removably attaches to and electrically communicates with the handheld monitor via a handheld connector 124. The handheld monitor 120 has a monitor mount connector (not visible) that allows the sensor 800 to communicate with the monitor 101. Blood parameter measurements responsive to the index sensor 800 are displayed on the handheld display 600 and/or the larger monitor display 700. A patient monitoring platform responsive to optical sensors among others and providing both handheld and standalone monitoring capabilities is available from Masimo Corporation, Irvine, Calif.

As shown in FIG. 1, an optical sensor 800 disposed of after a single patient use is relatively expensive. Reducing the number of sensor emitters may significantly reduce the cost of testing patients for some conditions, such as blood-loss. In an advantageous embodiment, at least two sensors are provided for medical use. A relatively inexpensive "index sensor" has a reduced set of emitters (fewer wavelengths) and measures a blood parameter, such as tHb, with a correspondingly lower resolution. A relatively expensive high resolution or "hi-res" sensor has an expanded set of emitters (more wavelengths) and measures blood parameters with greater accuracy. In an advantageous embodiment, described in further detail with respect to FIGS. 2-14 below, a total hemoglobin index system derives a unit-less tHb index that varies over time. A tHb index advantageously utilizes a less expensive index sensor with a minimal number of LED emitters so as to reduce disposable sensor costs during initial patient testing.

FIG. 2 illustrates total hemoglobin (tHb) index monitoring 200 that advantageously uses a fewer-LED (index) sensor 210 for an initial tHb test. A high resolution (hi-res) sensor 230 that uses more-LEDs is used only if tHb issues, such as potential internal bleeding, cannot be eliminated by the index sensor 210. Both the index sensor 210 and the hi-res sensor 230 are single-use, disposable sensors. The hi-res sensor 230 is substantially more expensive than the index sensor 250 due to LED costs. In a particular embodiment, the index sensor 210 uses four LEDs and the high-res sensor uses eight LEDs. A tHb index sensor embodiment is described in detail with respect to FIGS. 8-14, below. A hi-res sensor is described with respect to U.S. patent application Ser. No. 12/056,179 filed Mar. 26, 2008, titled Multiple Wavelength Optical Sensor, assigned to Masimo Corporation, Irvine, Calif. and incorporated in its entirety by reference herein.

As shown in FIG. 2, a total hemoglobin (tHb) index 200 embodiment begins with a tHb measurement request 201 initially fulfilled with a tHb index sensor 210. The relatively low cost, low resolution index sensor is advantageously utilized to derive a dimensionless trend 211. For example, a stable trend over a sufficiently long period of time may be sufficient assurance to a care provider that further testing is unnecessary, as described with respect to FIG. 3, below. Dimensionless tHb trend displays are described with respect to FIGS. 6-7, below.

Also shown in FIG. 2, if a tHb trend is inconclusive 212, a care provider may request a high-resolution sensor 230. If noninvasive measures fail to yield a definitive diagnosis, an invasive blood draw 260 and corresponding laboratory analysis is utilized alone or in addition to continuous high resolution sensor measurements for a definitive tHb assessment. Appropriate patient therapy 252 may include follow-up surgery and blood transfusion.

Figure 3A:
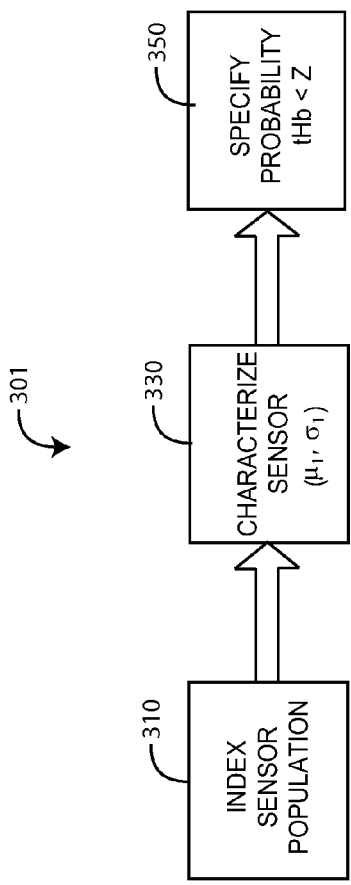
FIGS. 3A-B are a tHb index sensor characterization flow diagram and a corresponding sensor characterization graph.
Figure 3B:
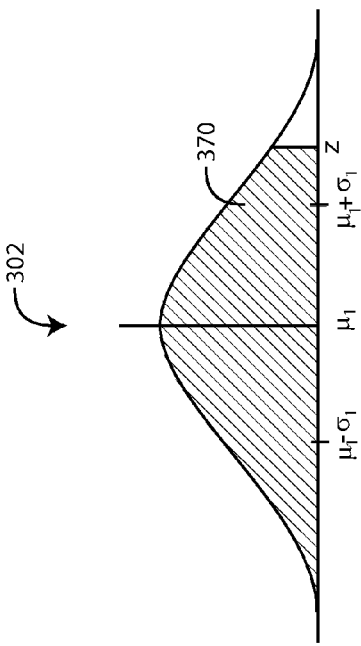

FIGS. 3A-B illustrate a tHb index sensor method including a characterization flow diagram 301 and a corresponding sensor characterization graph 302. As shown in FIG. 3A, a statistically-significant population of index tHb sensors 310 is characterized 330 by measuring the mean ($\mu_1$) and standard deviation ($\sigma_1$) of a Gaussian-distributed population of tHb measurements. The corresponding z score of the index sensors 350 is calculated as:

$$Z = \frac{x - \mu_1}{\sigma_1} \qquad \text{EQ. 1}$$

As shown in FIG. 3B, the probability that a tHb measurement for a given index sensor is less than z is the shaded area 370 of a normal distribution having a mean $\mu_1$ and a standard deviation $\sigma_1$. For example, from a standard statistical table, a z value of 1.28 indicates a 89.97% (~90%) probability that the measured value is less than z. Use of a index sensor z value for initial tHb index 210 (FIG. 2) is described in further detail with respect to FIG. 5, below.

Figure 4B:
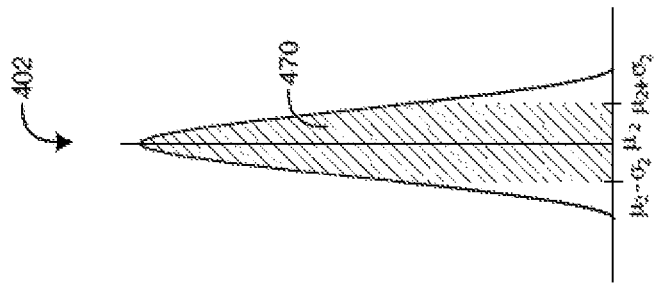
FIGS. 4A-B are a tHb high-resolution sensor characterization flow diagram and corresponding sensor characterization graph.
Figure 4A:
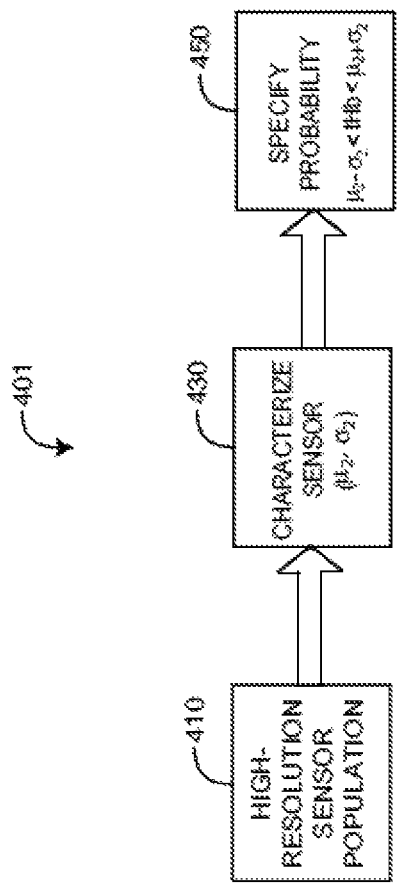

FIGS. 4A-B illustrate a high-resolution tHb sensor characterization method including a characterization flow diagram 401 and a corresponding sensor characterization graph 402. As shown in FIG. 4A, a statistically-significant population of high-resolution tHb sensors 410 is characterized 430 by measuring the mean ($\mu_2$) and standard deviation ($\sigma_2$) of a Gaussian-distributed population of tHb measurements. The corresponding accuracy of the high-resolution sensor is calculated as:

$$tHb = \mu_2 \pm \sigma_2 \qquad \text{EQ. 2}$$

As shown in FIG. 4B, the probability that a tHb measurement for a given high-resolution sensor is within one standard deviation of the mean is 68%. Use of a high-resolution sensor tHb measurement is described in further detail with respect to FIG. 5, below.

Figure 5:
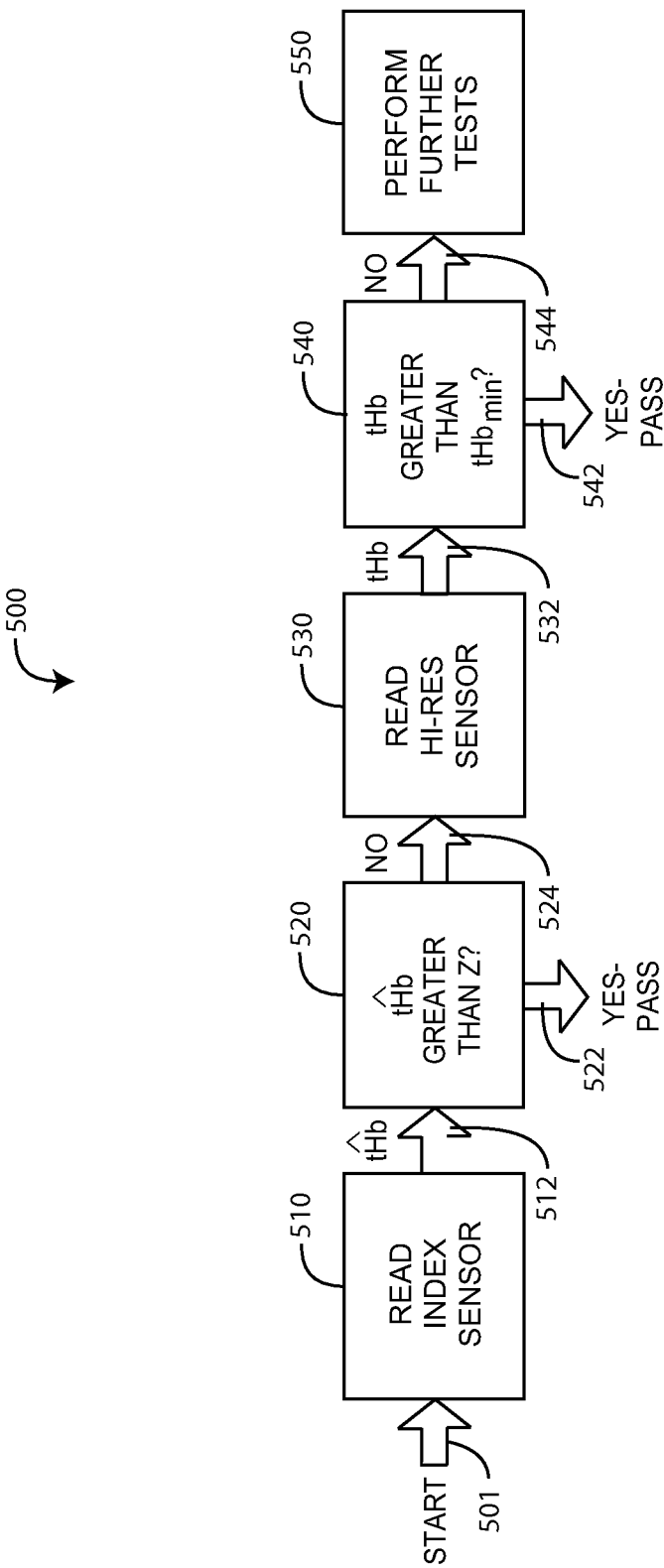
FIG. 5 is a detailed flow diagram of tHb testing utilizing a combination of index and high-resolution disposable optical sensors.

FIG. 5 further illustrates tHb testing 500 utilizing a combination of a disposable index sensor and a disposable high-resolution sensor. Initially, a disposable tHb index sensor is attached to a patient and a corresponding monitor 101 (FIG. 1). The monitor reads the index sensor 510 to obtain a total hemoglobin estimate $\hat{tHb}$. That estimate is compared with the z-value 520, as described with respect to EQ. 1, above. If the total hemoglobin estimate is greater than z, then the patient has a sufficiently high tHb to pass the test 522, i.e. to eliminate low tHb and issues regarding low tHb (such as internal bleeding) as a concern. In an embodiment, z is chosen so that the probability that tHb is too low is approximately 90%. Advantageously, use of a relatively inexpensive, minimally emitter-populated index sensor at this stage of patient testing provides a significant cost-saving over time and encourages more frequent use of noninvasive tHb testing as a patient care standard.

Further shown in FIG. 5, in the event $\hat{tHb}$ is less than z 524 then tHb is retested utilizing a disposable high resolution sensor 530. If tHb is greater than $tHb_{min}$, then the patient has a sufficiently high tHb to pass the test 542. Advantageously, even though a second, more expensive fully emitter-populated high-resolution sensor is used during this second stage test, this multistage test is configured to have an overall cost savings as compared to solely using high-resolution sensors. Although an index sensor test described above is based upon a z-value, other tHb threshold measures may be used. As an example, a fraction of or multiplier of z may be used to calculate the index sensor threshold.

Traditional invasive lab testing provides delayed results and requires a painful needle stick and time-consuming blood draws. A total hemoglobin (tHb) index system incorporating an advantageous noninvasive, disposable sensor and a monitor advantageously calculating and displaying a tHb index facilitates timely patient assessment and reduces the need to wait for lab results.

Also, noninvasive tHb monitoring advantageously provides real-time visibility to changes, or lack of changes, in total hemoglobin between invasive blood sampling. Continuous, real-time tHb monitoring is particularly advantageous when a tHb trend is stable and a clinician may otherwise think tHb is dropping; a tHb trend is rising and the clinician may otherwise think tHb is not rising fast enough; or the tHb trend is dropping and the clinician may otherwise think tHb is stable.

Figure 6:
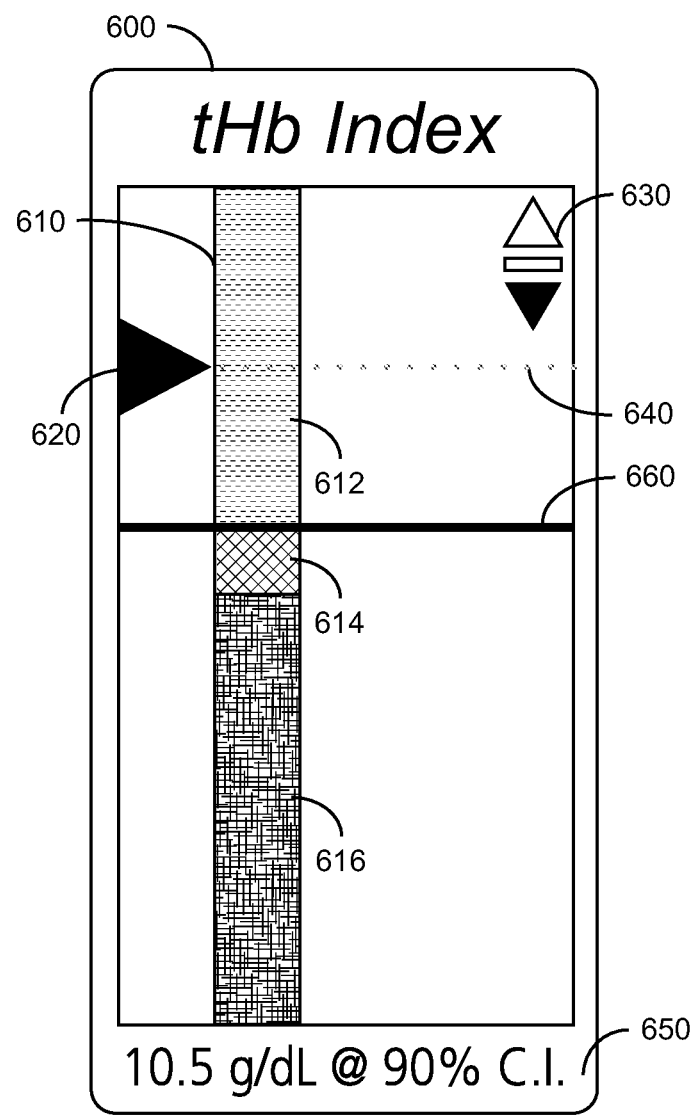
FIG. 6 is a handheld-monitor tHb index display.
Figure 7:
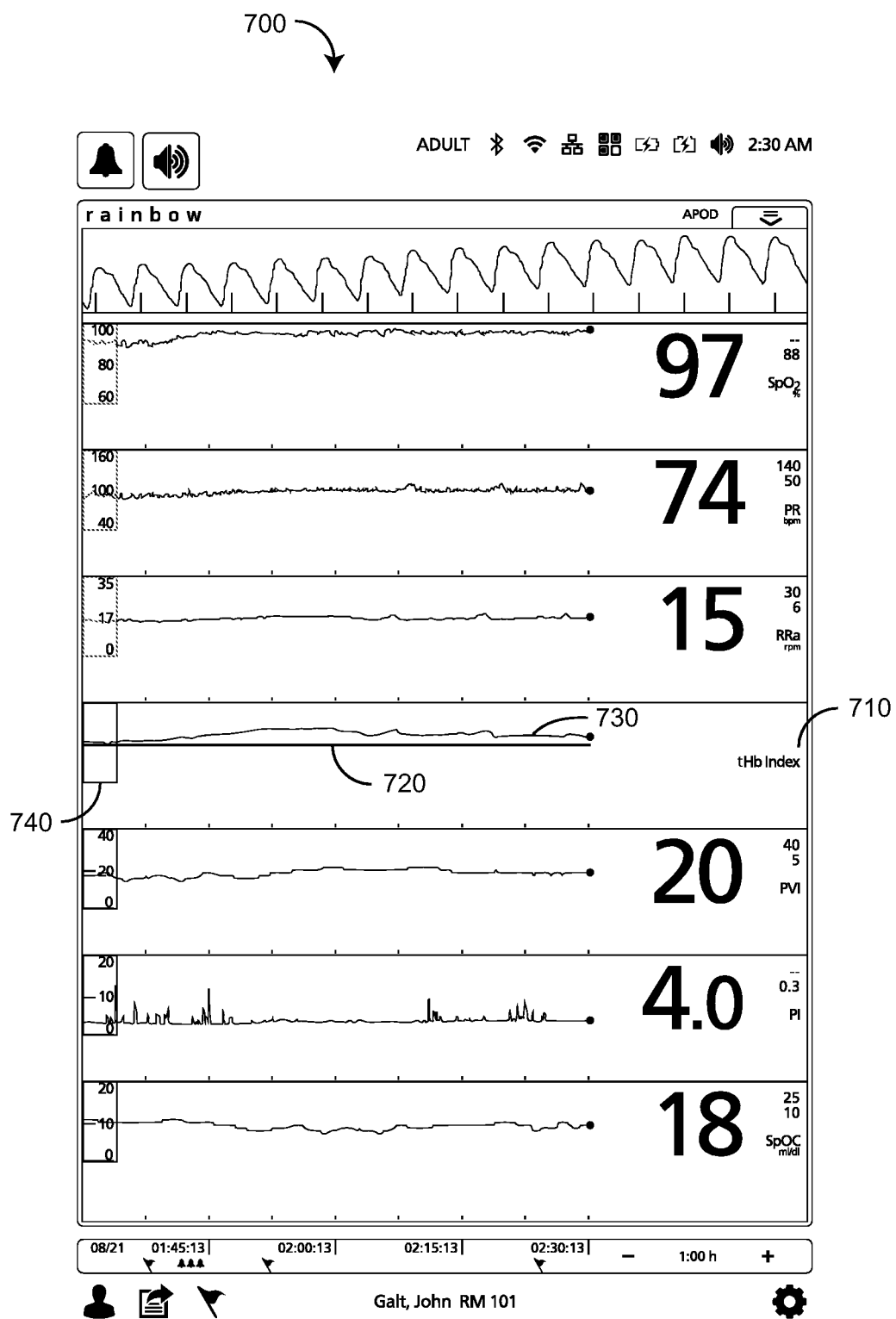
FIG. 7 is a multi-parameter monitor display illustrating a tHb index in conjunction with various other pulsatile blood flow parameters.

FIGS. 6-7 illustrate advantageous graphical index measures of total hemoglobin (tHb index) that address the need to provide real-time visibility to changes while using a relatively inexpensive tHb index sensor. FIG. 6 illustrates a tHb index display 600 embodiment advantageously suited for a relatively small area display, such as on a handheld monitor 120 (FIG. 1). In particular, the handheld tHb index has no time axis. Instead, a vertical bar graph 610 has dimensionless green 612, yellow 614 and red 616 zones for indicating a range of relative tHb values. The present relative value of a tHb index is indicated by a vertical-ranging pointer 620 and a dotted line 640 extending horizontally across the display 600. A horizontal line 660 is disposed across the width of the display between the green zone 612 and yellow zone 614. A tHb value 650 is listed at the display bottom, e.g. "10.5 g/dL@ 90% C.I." Accordingly, the horizontal line 660 represents 10.5 g/dl and a corresponding 90% confidence interval that the present tHb value is greater than 10.5 g/dL. In this example, the yellow zone 614 represents a 10% likelihood the present tHb value is less than 10.5 g/dL. Although the tHb index display has no time axis, a trend indicator 630 has up arrow, horizontal line and down arrow symbols. The current tHb index trend is indicated by a highlighted one of these symbols.

FIG. 7 illustrates a multi-parameter monitor display 700 including such parameters as oxygen saturation, pulse rate, respiration rate, tHb index 710, pulse variability index (PVI), perfusion index (PI) and oxygen content (SpOC) versus time. An advantageous tHb index versus time display 710 has no listed parameter range 740. However, a baseline tHb value 720 is displayed as a horizontal line and a time varying tHb index 730 is displayed relative to the baseline 720. The baseline 720 is set at a tHb value and corresponding confidence interval, as described with respect to FIG. 6, above.

Figure 8A:
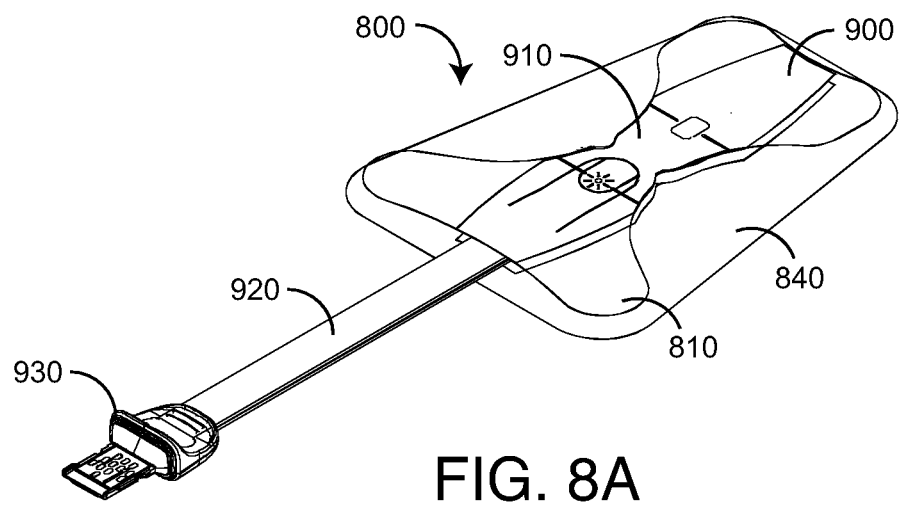
FIGS. 8A-B are perspective and top views, respectively, of a tHb index sensor.
Figure 8B:
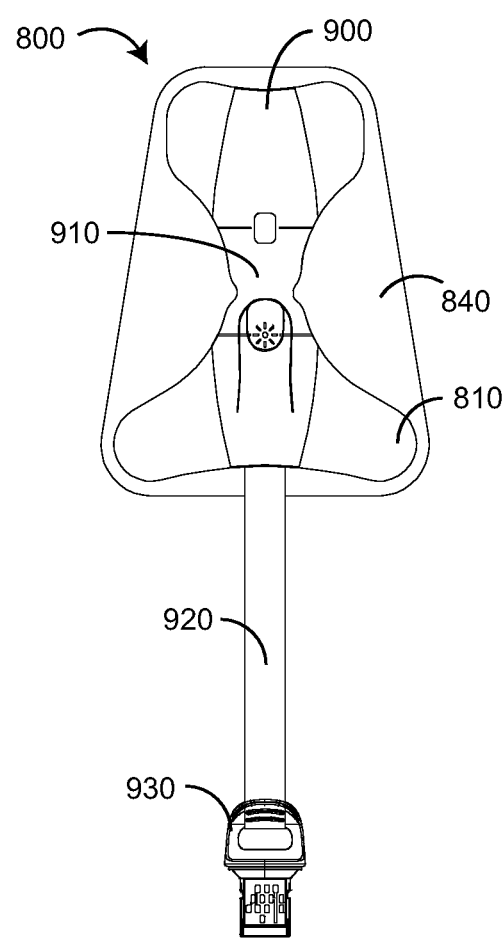

FIGS. 8A-B generally illustrate a disposable index sensor 800 that removably attaches to a fingertip and electrically interconnects to a physiological monitor as shown and described with respect to FIG. 1, above. The sensor 800 has an adhesive butterfly wrap 810, a head assembly 900 and a release liner 840. The head assembly 900 has a sensor head 910, a connector 930 and an insulated interconnect 920. The interconnect 920 provides mechanical and electrical communications between the sensor head 910 and the connector 930. The release liner 840 is removed from the adhesive butterfly wrap 810 so as to attach the sensor head 910 to a fingertip 1 (FIG. 1). A connector 930 inserts into a corresponding patient cable socket 132 (FIG. 1) so as to provide communications between the sensor 800 and a standalone monitor 101 (FIG. 1) or portable handheld monitor 120 (FIG. 1).

FIGS. 9A-E further illustrate the head tape assembly 900 including a first head tape side (FIG. 9A), a second head tape side (FIG. 9B), a detector window 912 (FIG. 9C) exposing the detector 1200, an emitter window 914 (FIG. 9D) exposing the emitter 1100 and a connector 935 (FIG. 9E) schematic view, respectively, for a tHb index sensor. As shown in FIG. 9A, the first head tape side has an imprinted fingernail target 906 on a bottom half 905. As shown in FIG. 9B, the second head tape side has an imprinted finger pad target 909 on a top half 908 and a printed fold line 907 separating the top half 908 and bottom half 905. The sensor head 910 (FIGS. 8A-B) is attached to a fingertip site by placing the fingernail target 906 over a fingernail, folding the sensor head at the fold line 907 and over the fingertip so as to place the finger pad target on a finger pad. The sensor head 910 is then held in place by folding the butterfly wrap 810 (FIGS. 8A-B) around the finger 800 (FIG. 1).

As shown in FIG. 9E, the connector 930 (FIG. 9A) and in particular, the connector contacts 935 allow a monitor to sequentially activate the LEDs 1100, which illuminate a fingertip with red and IR wavelengths. The detector 1200 is responsive to the wavelengths after attenuation by pulsatile blood flow within the fingertip. The monitor analyzes the detector signal so as to measure blood constituents including tHb. The monitor may also read an EEPROM 990 and resistor 970 mounted in the connector 930 so as to identify the sensor 800 (FIGS. 8A-B).

Figure 10:
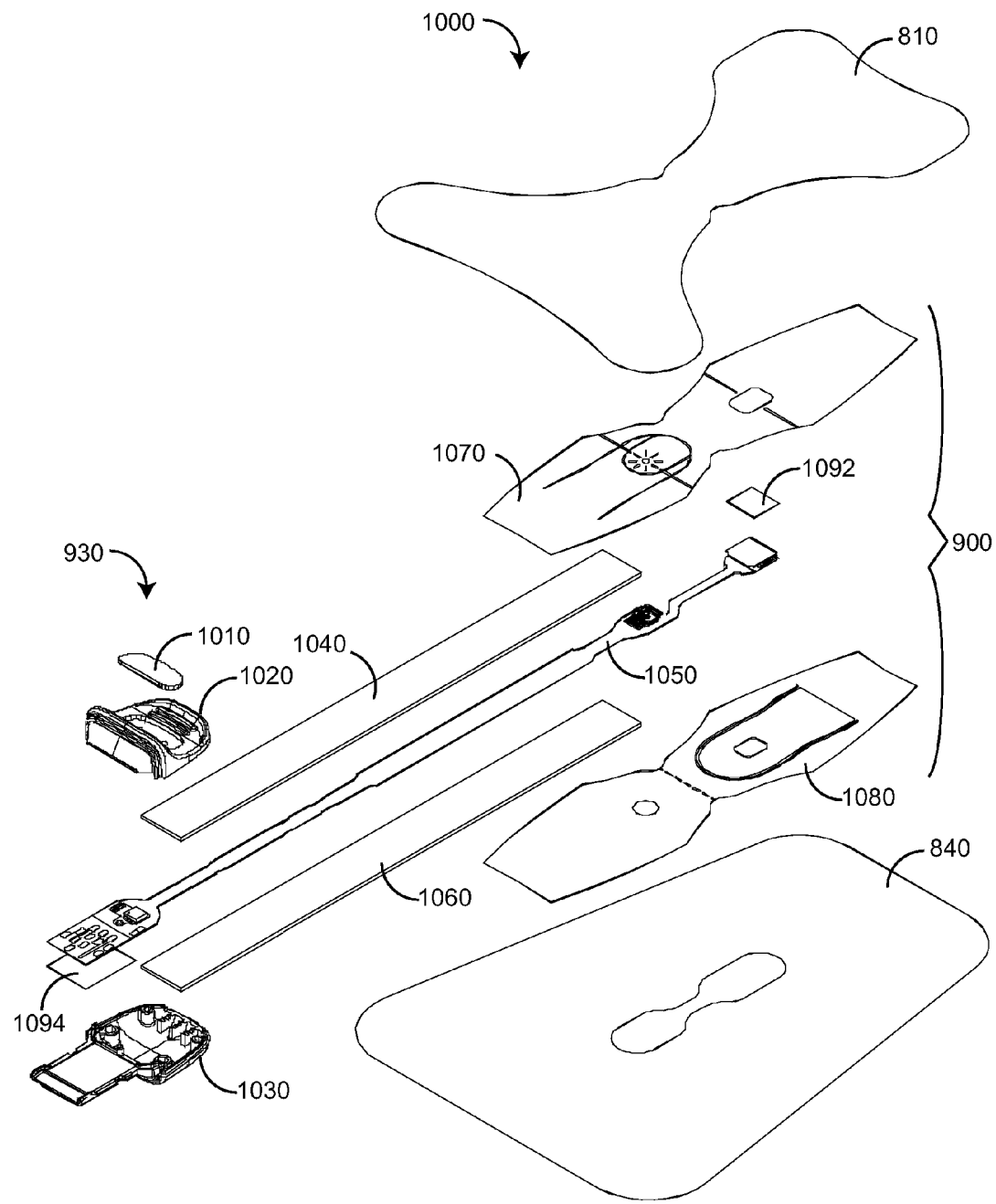
FIG. 10 is an exploded view of a tHb index sensor.

FIG. 10 further illustrates the tHb index sensor described above with respect to FIGS. 8-9. The tHb index sensor 1000 (800 FIGS. 8A-B) has an adhesive butterfly wrap 810, a top head tape 1070, a polyethylene foam tape insulator 1040, 1060, a flex circuit assembly 1050, a bottom head tape 1080 and a release liner 840. The sensor connector 930 has an LED label 1010 identifying this as a index sensor, a connector top shell 1020, a sensor bottom shell 1030 and adhesives 1092, 1094.

FIGS. 11-13 illustrate in detail the optical elements of a tHb index sensor 800 (FIGS. 8A-B), including an emitter 1100 that sequentially illuminates a fleshy tissue site, such as a fingertip, with four discrete wavelengths of optical radiation and a detector 1200 that is responsive to the optical radiation after absorption by pulsatile blood flow within the tissue site. A monitor 100 (FIG. 1) has processors responsive to the detector 1200 so as to derive an indication of one or more blood constituents, such as a tHb trend described with respect to FIGS. 6-7 above.

As shown in FIGS. 11A-D, an emitter 1100 has an encapsulant 1110 housing a lead frame 1120 and emitter dice 1130 mounted and wire bonded to the lead frame 1120. As shown in FIGS. 12A-D, a detector 1200 has an encapsulant 1210 housing a lead frame 1220 and a detector die 1230 mounted and wire bonded to the lead frame 1220. The emitter 1100 and detector 1200 are mounted via their respective lead frames 1120, 1220 to a flex circuit assembly 1050 (FIG. 10), as described above, so as to respond to emitter drive signals from a monitor via a connector 935 (FIG. 9E) and to transmit detector signals to a monitor via the connector 935 (FIG. 9E).

Figure 13A:
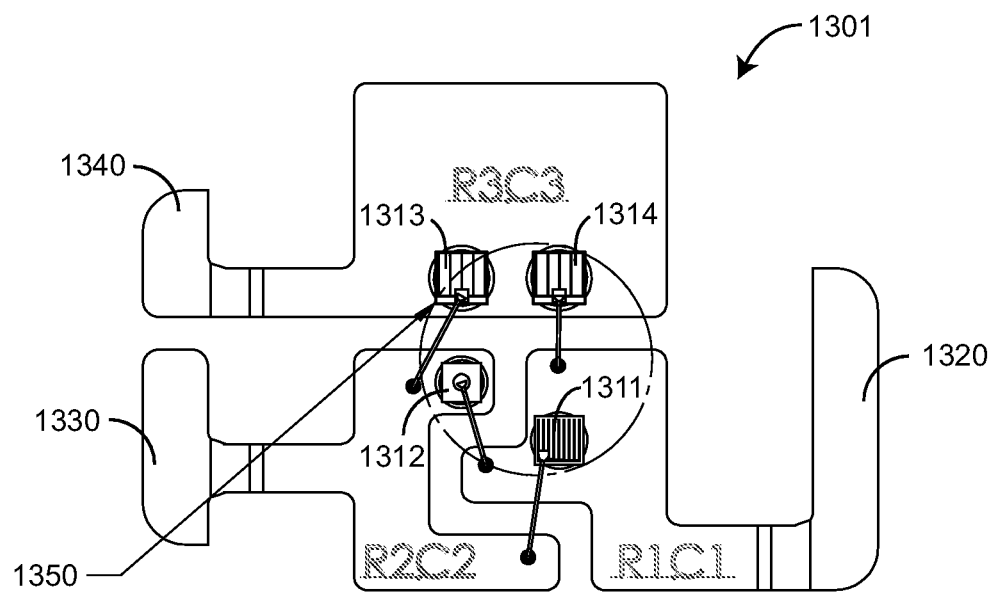
FIGS. 13A-B are LED layout and corresponding emitter schematic views of an emitter assembly.
Figure 13B:
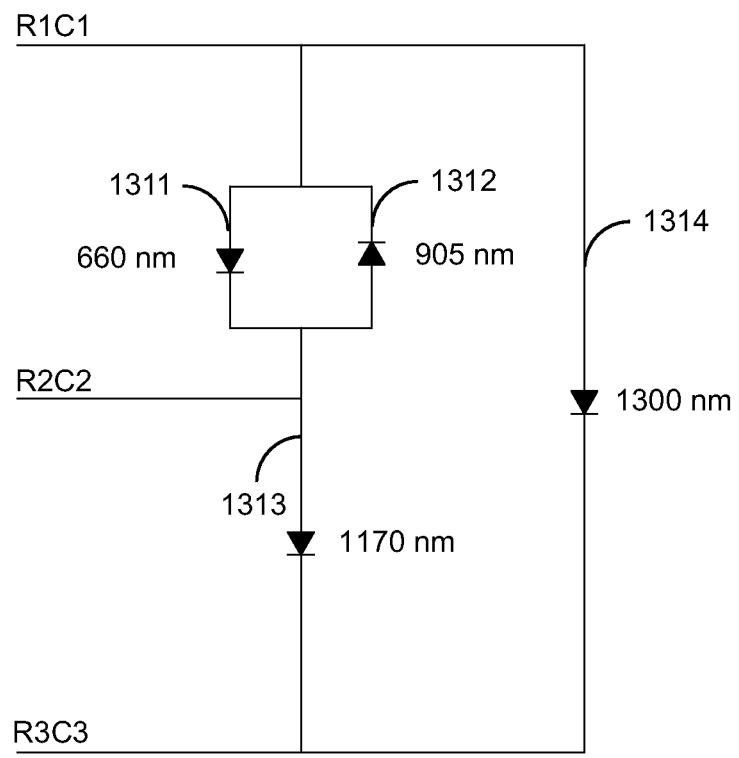

As shown in FIGS. 13A-B, in a 4-wavelength embodiment, LEDs are mounted on a lead frame 1301 having three leads 1320, 1330, 1340. Four LED die 1311-1314 are each mounted on one face and wire bonded on an opposite face to various lead frame pads R1C1, R2C2, R3C3 proximate an emitter optical center 1350. In a particular embodiment, the LEDs emit light at 660 nm, 905 nm, 1170 nm and 1300 nm.

Figure 14A:
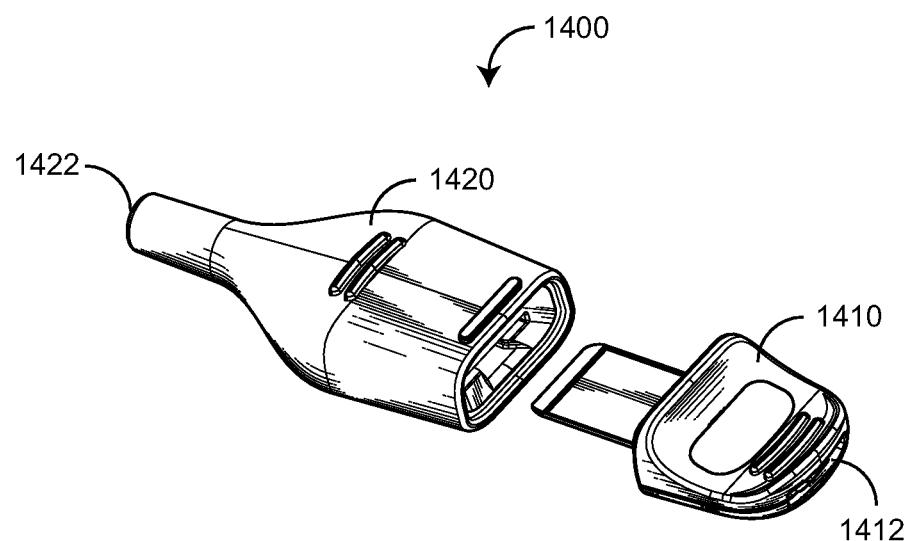
FIGS. 14A-B are a socket and plug perspective view and a socket and plug perspective cutaway view of a pogo pin connector assembly.
Figure 14B:
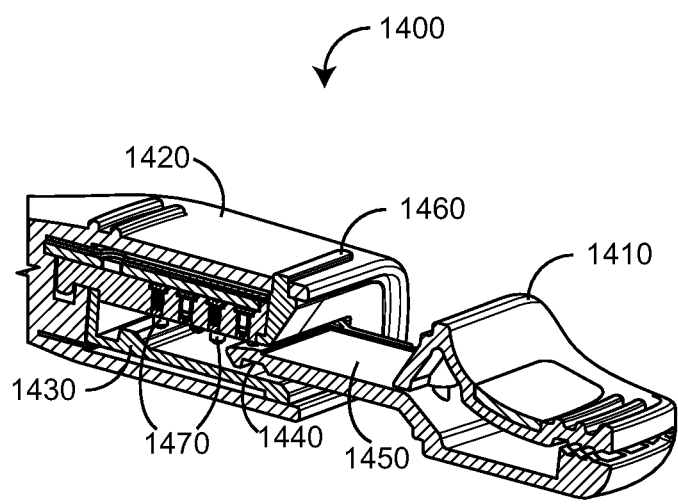

FIGS. 14A-B illustrate a pogo pin sensor connector assembly. As shown in FIG. 14A, the connector assembly 1400 has a plug 1410 that accepts flex circuit conductors via a generally elongated aperture 1412 and a socket 1420 that accepts cable conductors via a generally round aperture 1422. A plug shelf 1450 provides a generally solid, flat surface for fixedly mounting flex circuit connector pads e.g. 935 (FIG. 9A), which are inserted into the socket 1420. The plug 1410 provides a sensor connector e.g. 810 (FIG. 1) and the socket 1420 provides a monitor cable connector 132 (FIG. 1) so as to allow a monitor and sensor to electrically communicate drive signals and sensor signals as described above.

As shown in FIG. 14B, when the plug 1410 is fully inserted into the socket 1420, a plug latch 1440 engages a socket catch 1430 removably securing the plug 1410 to the socket 1420. Spring-mounted pogo pins 1470 in the socket 1420 mechanically and electrically engage flex circuit pads on the plug 1410 so as to electrically interconnect flex circuit and cable conductors. A release 1460 disengages the catch 1430 and latch 1440 allowing the plug 1410 to be removed from the socket 1420.

A total hemoglobin index system has been disclosed in detail in connection with various embodiments. These embodiments are disclosed by way of examples only and are not to be construed as limiting the scope of the claims that follow. One of ordinary skill in art will appreciate many variations and modifications.

What is claimed is:

1. A system for measuring total hemoglobin in a patient comprising:
    a first optical sensor configured to measure a blood parameter with a first resolution, the first optical sensor including:
        a first plurality of emitters and a first detector;
        a first attachment configured to dispose the first plurality of emitters and the first detector proximate a tissue site having pulsatile blood flow; and
        a first sensor connector in electrical communications with the first plurality of emitters and the first detector;
    a second optical sensor configured to measure the blood parameter with a second resolution, the second optical sensor including:
        a second plurality of emitters and a second detector, wherein the second plurality of emitters comprises more emitters than the first plurality of emitters in the first optical sensor and the second resolution of the second optical sensor is greater than the first resolution of the first optical sensor;
        a second attachment configured to dispose the second plurality of emitters and the second detector proximate the tissue site having pulsatile blood flow; and
        a second sensor connector in electrical communications with the second plurality of emitters and the second detector;
    a monitor configured to communicate with at least one of the first optical sensor and the second optical sensor via the first and second sensor connectors, the monitor further configured to:
        measure a first total hemoglobin estimate at the first resolution using the first optical sensor; and
        if the first total hemoglobin estimate is below a predetermined threshold, provide an indication to a user to attach the second optical sensor to the patient and measure a second total hemoglobin estimate at the second resolution.

2. The system according to claim 1 wherein the first plurality of emitters of the first optical sensor comprise four LEDs and the second plurality of emitters of the second optical sensor comprise eight LEDs.

3. The system according to claim 2 wherein the four LEDs of the first optical sensor are mounted on a three-lead common carrier.

4. The system according to claim 3 wherein a first one of the four LEDs is connected between a first lead and a second lead of the common carrier.

5. The system according to claim 4 wherein a second one of the four LEDs is connected between the first lead and the second lead in a polarity opposite of the first LED.

6. The system according to claim 5 wherein a third one of the four LEDs is connected between the second lead and the third lead of the common carrier.

7. The system according to claim 6 wherein the four LEDs are activated by sequentially applying a voltage between any two of the three leads.

8. The system according to claim 2 wherein the four LEDs of the first optical sensor comprise 660 nm, 905 nm, 1170 nm and 1300 nm wavelengths.

9. The system of claim 1, wherein the monitor is further configured to generate a total hemoglobin index display comprising the first total hemoglobin estimate.

10. The system of claim 9, wherein the total hemoglobin index display of the monitor has no time axis and further comprises a vertical bar graph for indicating a range of relative total hemoglobin values.

11. The system of claim 10, wherein the total hemoglobin index display further comprises a pointer configured to move vertically so as to indicate a present total hemoglobin index value.

12. The system of claim 11, wherein the total hemoglobin index display further comprises a trend indicator.

13. A method for measuring total hemoglobin in a patient, the method comprising:
   attaching a first optical sensor to the patient, the first optical sensor comprising:
      a first plurality of emitters and a first detector; and
      a first attachment configured to dispose the first plurality of emitters and the first detector proximate a tissue site having pulsatile blood flow;
   measuring a first total hemoglobin estimate at a first resolution using the first optical sensor; and
   if the first total hemoglobin estimate is below a predetermined threshold, providing an indication to a user to attach a second optical sensor to the patient and measuring a second total hemoglobin estimate at a second resolution, wherein the second optical sensor comprises:
      a second plurality of emitters and a second detector, wherein the second plurality of emitters comprises more emitters than the first plurality of emitters in the first optical sensor and the second resolution of the second optical sensor is greater than the first resolution of the first optical sensor;
      a second attachment configured to dispose the second plurality of emitters and the second detector on the opposite portions of the tissue site having pulsatile blood flow.

14. The method according to claim 13 wherein measuring the first total hemoglobin estimate comprises sequentially transmitting 660 nm, 905 nm, 1170 nm and 1300 nm wavelengths from the first optical sensor into a fingernail portion of the tissue site.

15. The method according to claim 14 wherein receiving measuring the first total hemoglobin estimate further comprises:
   detecting the wavelengths at the fingernail portion of the tissue site;
   generating a sensor signal responsive to the detected wavelengths; and
   transmitting the sensor signal to a monitor.

16. The method according to claim 15 further comprising:
   analyzing the sensor signal to determine a total hemoglobin trend; and
   graphically showing the total hemoglobin trend on a display of the monitor.

17. The method of claim 16, wherein the display of the monitor has no time axis and comprises a vertical bar graph for indicating a range of relative total hemoglobin values.

18. The method of claim 17, wherein the display further comprises a pointer configured to move vertically so as to indicate a present total hemoglobin index value.

19. The method of claim 18, wherein the display further comprises a trend indicator.

20. The method according to claim 13, wherein the first plurality of emitters comprises four LEDs and the second plurality of emitters comprises eight LEDs.

* * * * *